(12) United States Patent
Dalena et al.

(10) Patent No.: US 11,696,811 B2
(45) Date of Patent: Jul. 11, 2023

(54) MEDICAL DEVICE TRANSPORTATION SYSTEMS

(71) Applicant: Boston Scientific Scimed, Inc., Maple Grove, MN (US)

(72) Inventors: Michele E. Dalena, Boston, MA (US); Lisa Spak, Manchester, CT (US); William J. Schnell, Middleville, MI (US); Jason D. Holt, Flower Mound, TX (US); Kyle P. Moore, Hopkinton, MA (US); Nathan T. Cummings, Worcester, MA (US); Jenny Dandin, Worcester, MA (US); Alyson Borzillo, Boston, MA (US); Ryan LaFlamme, Ham Lake, MN (US); Joshua Talsky, Brooklyn, NY (US); Mark Collins, Cedarburg, WI (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 17/123,754

(22) Filed: Dec. 16, 2020

(65) Prior Publication Data

US 2021/0186640 A1    Jun. 24, 2021

Related U.S. Application Data

(60) Provisional application No. 62/953,352, filed on Dec. 24, 2019.

(51) Int. Cl.
*A61B 50/36*        (2016.01)
*A61B 50/00*        (2016.01)

(52) U.S. Cl.
CPC ........ *A61B 50/36* (2016.02); *A61B 2050/002* (2016.02); *A61B 2050/0065* (2016.02)

(58) Field of Classification Search
CPC .............. A61B 50/36; A61B 2050/005; A61B 2050/314; A61B 2050/002; A61B 2050/0065

(Continued)

(56) References Cited

U.S. PATENT DOCUMENTS

| 5,732,821 A | 3/1998 | Stone et al. |
| 6,641,781 B2 | 11/2003 | Walta |

(Continued)

FOREIGN PATENT DOCUMENTS

| DE | 202009014228 U1 | 3/2010 |
| DE | 202016105248 U1 | 12/2016 |

(Continued)

OTHER PUBLICATIONS

"ETS Plus Secure Endoscope Transportation with Hygienic Focus", Olympus brochure EO428343EN (2017) 3 pages.

(Continued)

*Primary Examiner* — Steven A. Reynolds
(74) *Attorney, Agent, or Firm* — Seager, Tufte & Wickhem LLP

(57) ABSTRACT

A system for containing and transporting a medical device may include a container including a bottom face and surrounding side faces as a closed first end and an open second end to form an inner portion for receiving and retaining the medical device. The liner may be extendable over the side faces to line the inner portion of the container to an outer surface of the bottom face of the container. The liner may act as a protective barrier to the container to minimize contamination when receiving and/or retaining a used medical device. First and second covers may be removably attachable to the container, over the liner, to enclose a medical device therebetween. A first cover may have a color or marking indicating the medical device is "clean", while a (Continued)

second cover may have a color or marking indicating the medical device is "used".

20 Claims, 20 Drawing Sheets

(58) Field of Classification Search
    USPC ............................................. 206/363
    See application file for complete search history.

(56) References Cited

U.S. PATENT DOCUMENTS

| | | | |
|---|---|---|---|
| 6,749,063 B2 * | 6/2004 | Parker | A61B 50/30 |
| | | | 206/363 |
| 7,744,832 B2 | 6/2010 | Horacek et al. | |
| 8,042,688 B2 | 10/2011 | Parks et al. | |
| 8,561,820 B2 | 10/2013 | Kitt et al. | |
| 8,733,551 B2 | 5/2014 | Parker et al. | |
| 8,747,739 B2 * | 6/2014 | Parker | A61B 50/00 |
| | | | 422/294 |
| 8,789,695 B2 | 7/2014 | Mason | |
| 8,807,354 B2 | 8/2014 | Kitt et al. | |
| 8,939,287 B2 | 1/2015 | Markovitch | |
| 9,156,590 B2 * | 10/2015 | Colayco | B65D 65/466 |
| 9,265,578 B2 | 2/2016 | Dacey | |
| D818,841 S | 5/2018 | Newton | |
| D819,404 S | 6/2018 | Metaxatos et al. | |
| D819,409 S | 6/2018 | Newton | |
| 10,086,131 B2 | 10/2018 | Okihara | |
| 10,405,938 B2 | 9/2019 | Ramsey | |
| D891,777 S | 8/2020 | Newton | |
| 2006/0273084 A1 | 12/2006 | Baker et al. | |
| 2007/0215507 A1 | 9/2007 | Glenn et al. | |
| 2009/0321305 A1 * | 12/2009 | Watson | B65D 51/242 |
| | | | 206/703 |
| 2011/0192744 A1 * | 8/2011 | Parker | A61B 50/30 |
| | | | 206/363 |
| 2012/0152289 A1 | 6/2012 | Smith et al. | |
| 2013/0009606 A1 * | 1/2013 | Smith | A61B 50/20 |
| | | | 429/100 |
| 2015/0144515 A1 | 5/2015 | Chartres et al. | |
| 2015/0257632 A1 | 9/2015 | Ramsey | |
| 2015/0259122 A1 | 9/2015 | Parker | |
| 2016/0058518 A1 | 3/2016 | Mason | |
| 2017/0056122 A1 | 3/2017 | Ramsey | |
| 2018/0110580 A1 | 4/2018 | Hynes | |
| 2018/0134453 A1 | 5/2018 | Wassenburg | |
| 2019/0167824 A1 | 6/2019 | Rhodes et al. | |
| 2020/0205925 A1 | 7/2020 | Cummings et al. | |
| 2021/0186641 A1 | 6/2021 | Cummings et al. | |

FOREIGN PATENT DOCUMENTS

| | | |
|---|---|---|
| DE | 102017008894 A1 | 3/2018 |
| EP | 2501321 A2 | 9/2012 |
| EP | 3288437 A1 | 3/2018 |
| GB | 2525694 A | 11/2015 |
| WO | 03034936 A1 | 5/2003 |
| WO | 2015166240 A2 | 11/2015 |

OTHER PUBLICATIONS

"Medivators™ Cleanascope™ Transport & Short Term Storage System", MEDIVATORS—A Cantel Medical Company brochure (2015) 4 pages.

"SafeCAP® Endoscope Transport and Short-Term Storage System", ClinicalChoice brochure (2019) 2 pages.

International Search Report and Written Opinion, Application No. PCT/US2019/068487, dated Apr. 22, 2020, 11 pages.

* cited by examiner

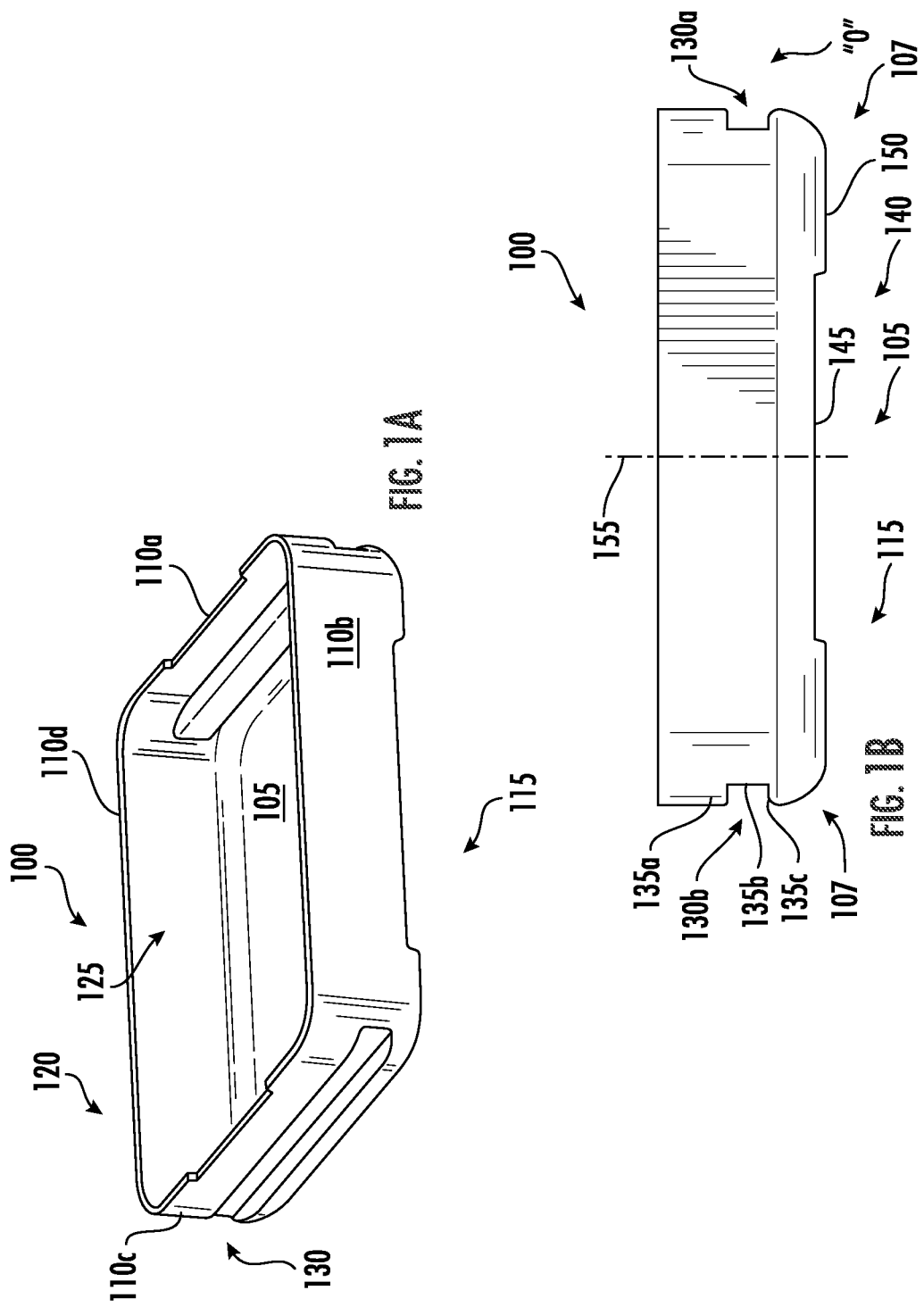

SECTION E-E

SECTION H-H

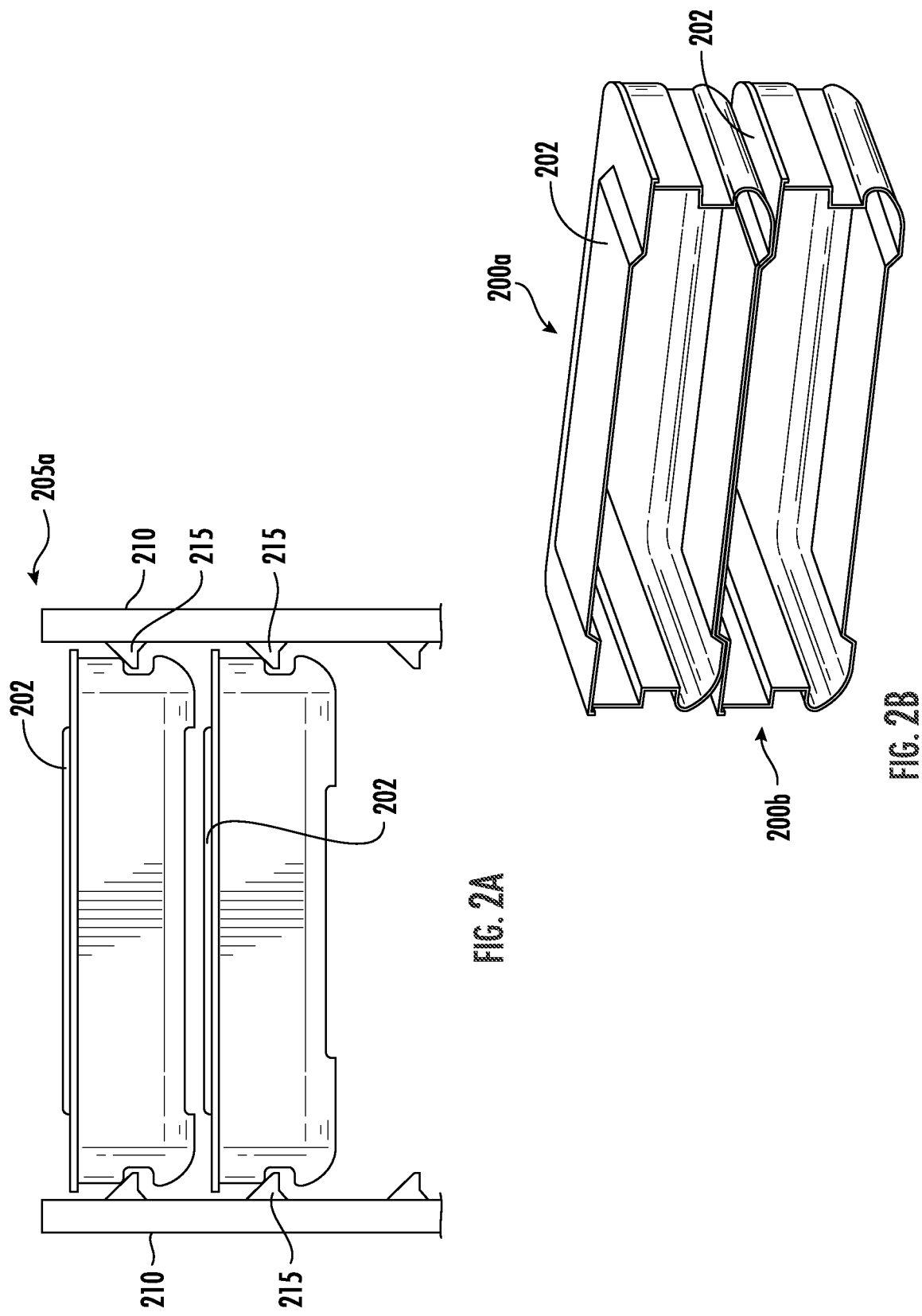

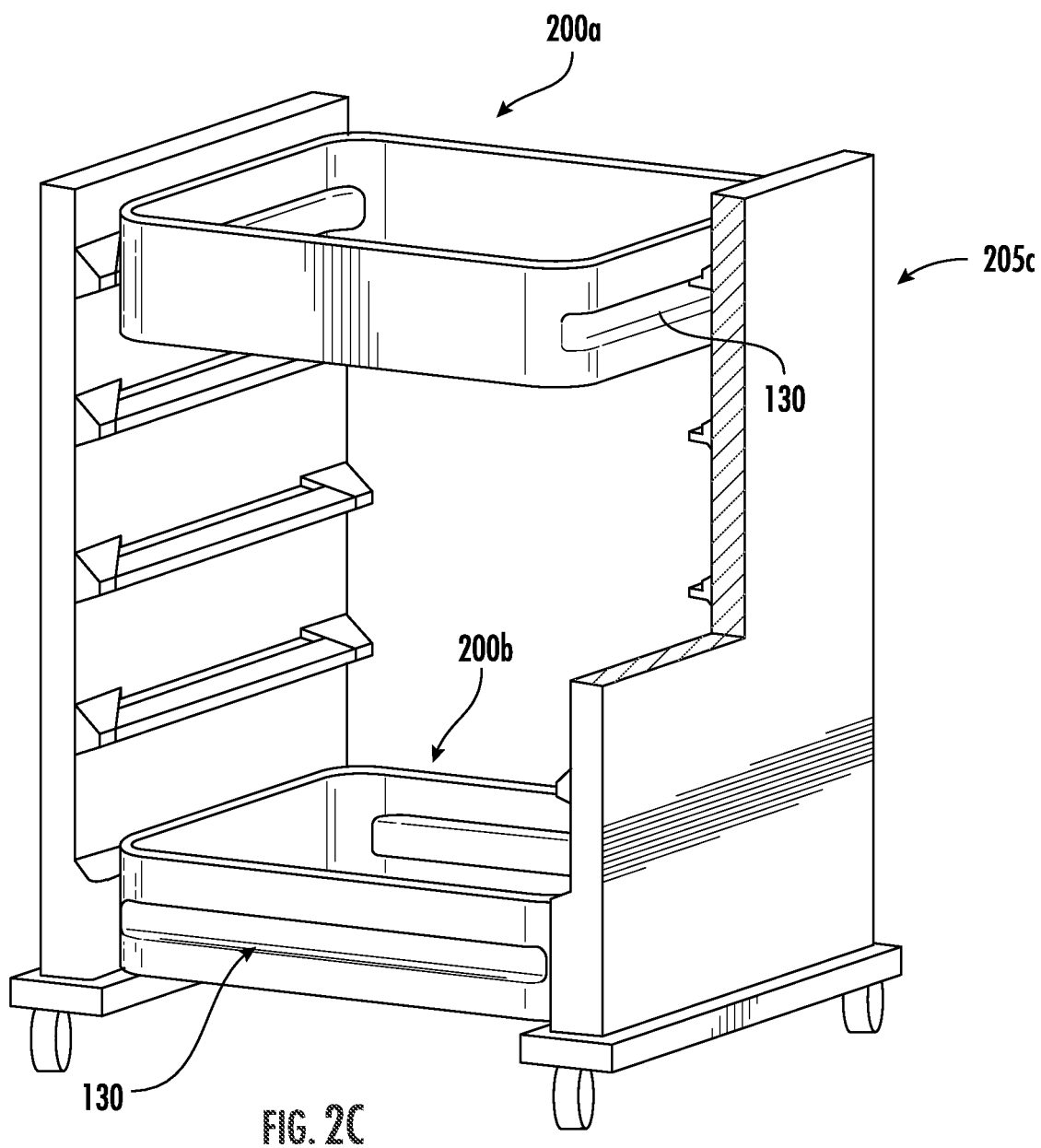

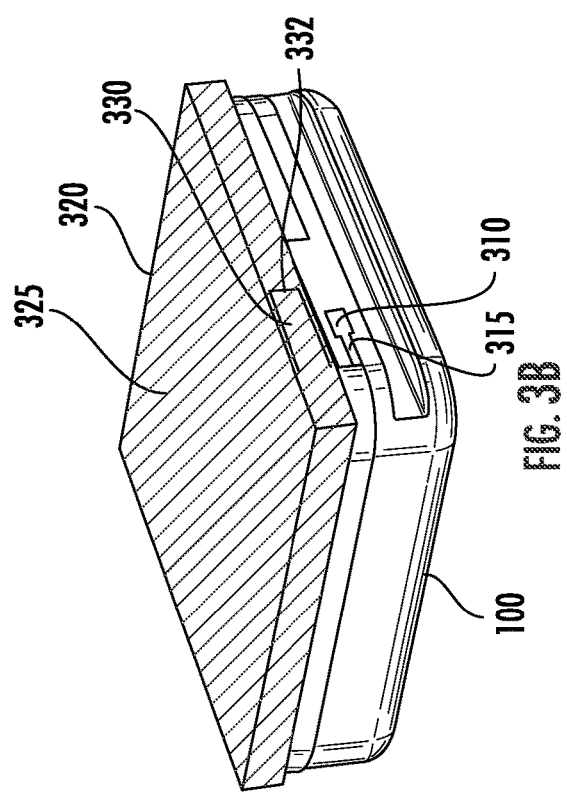
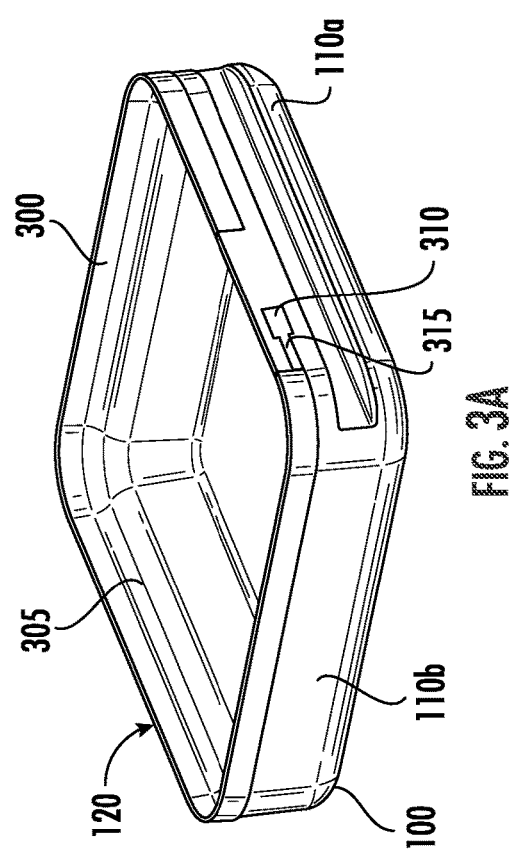
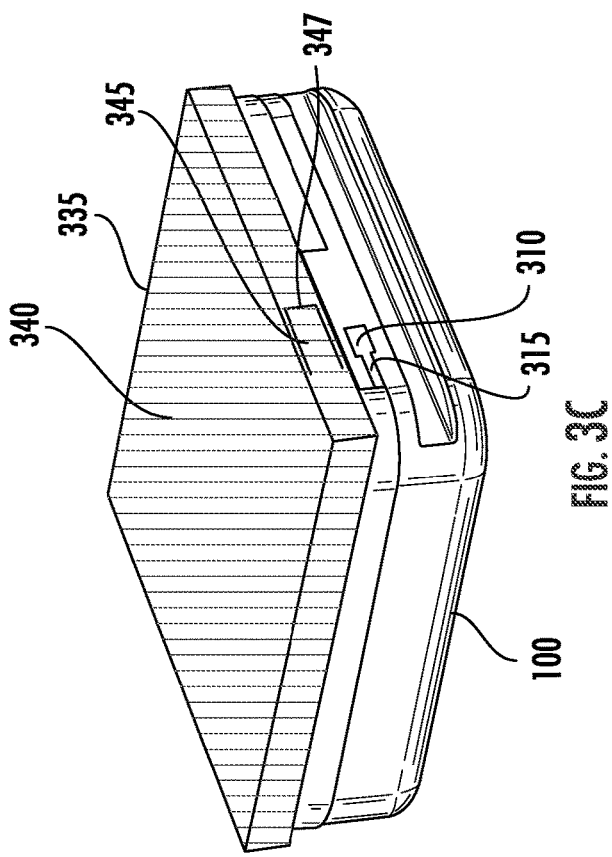

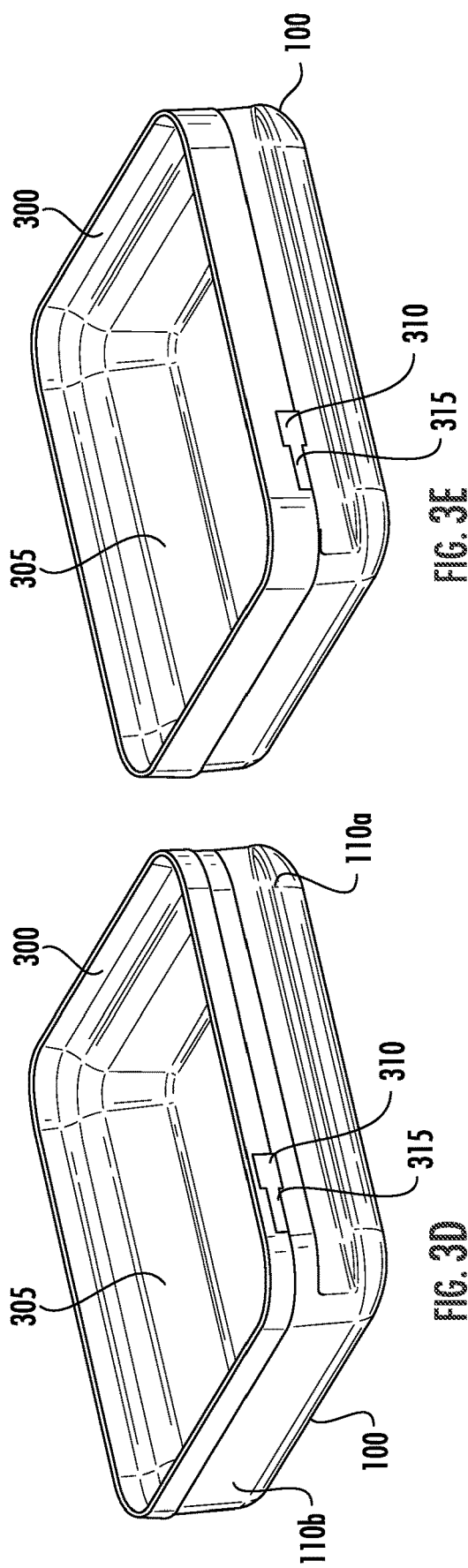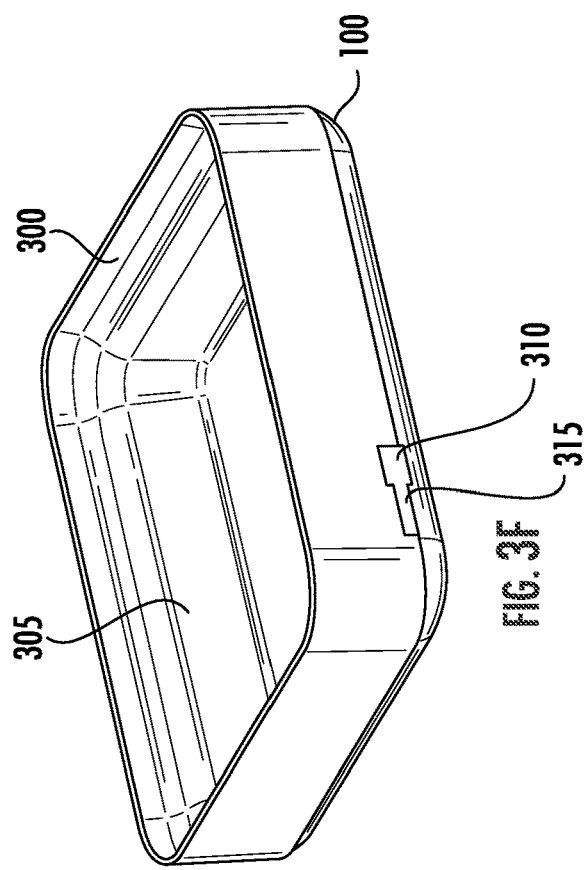

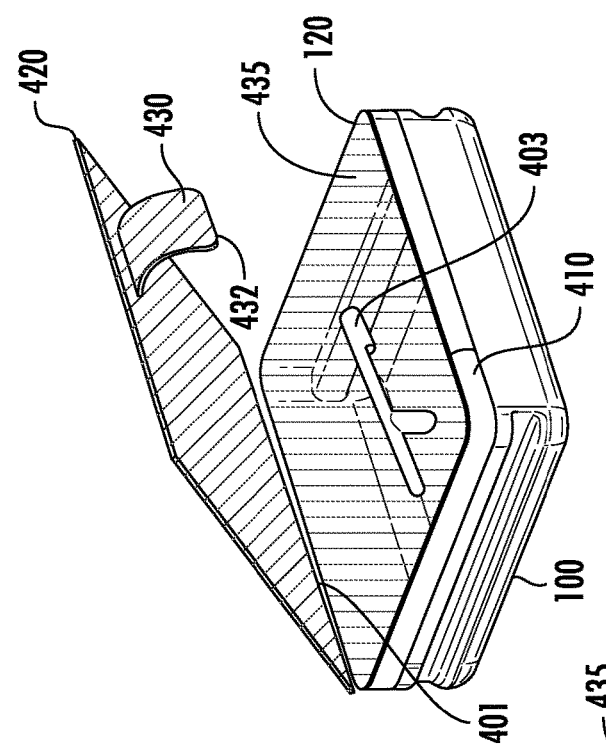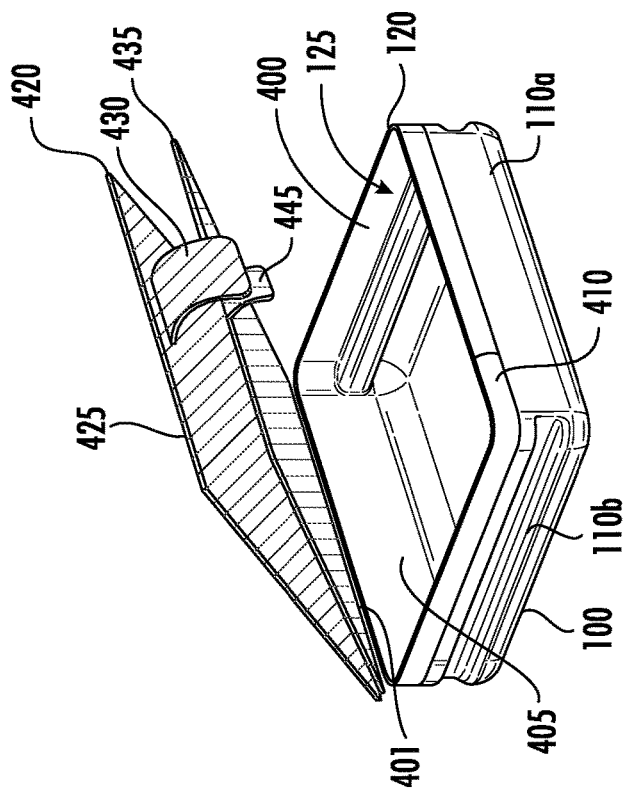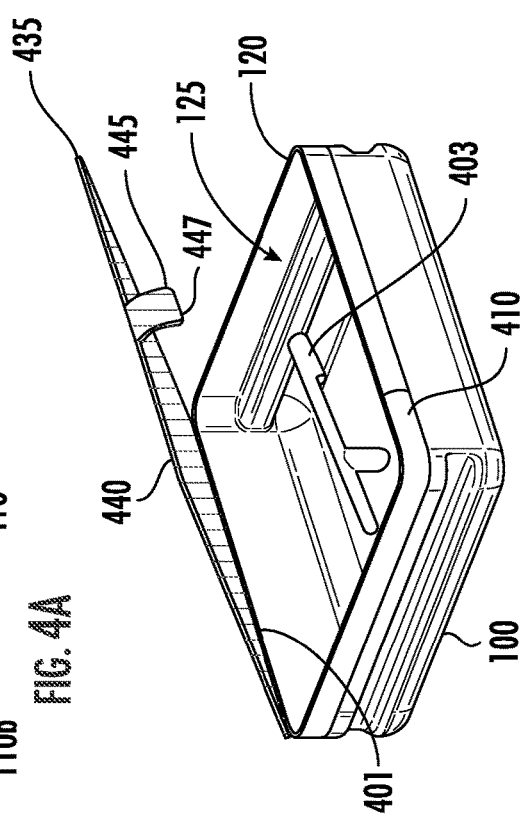

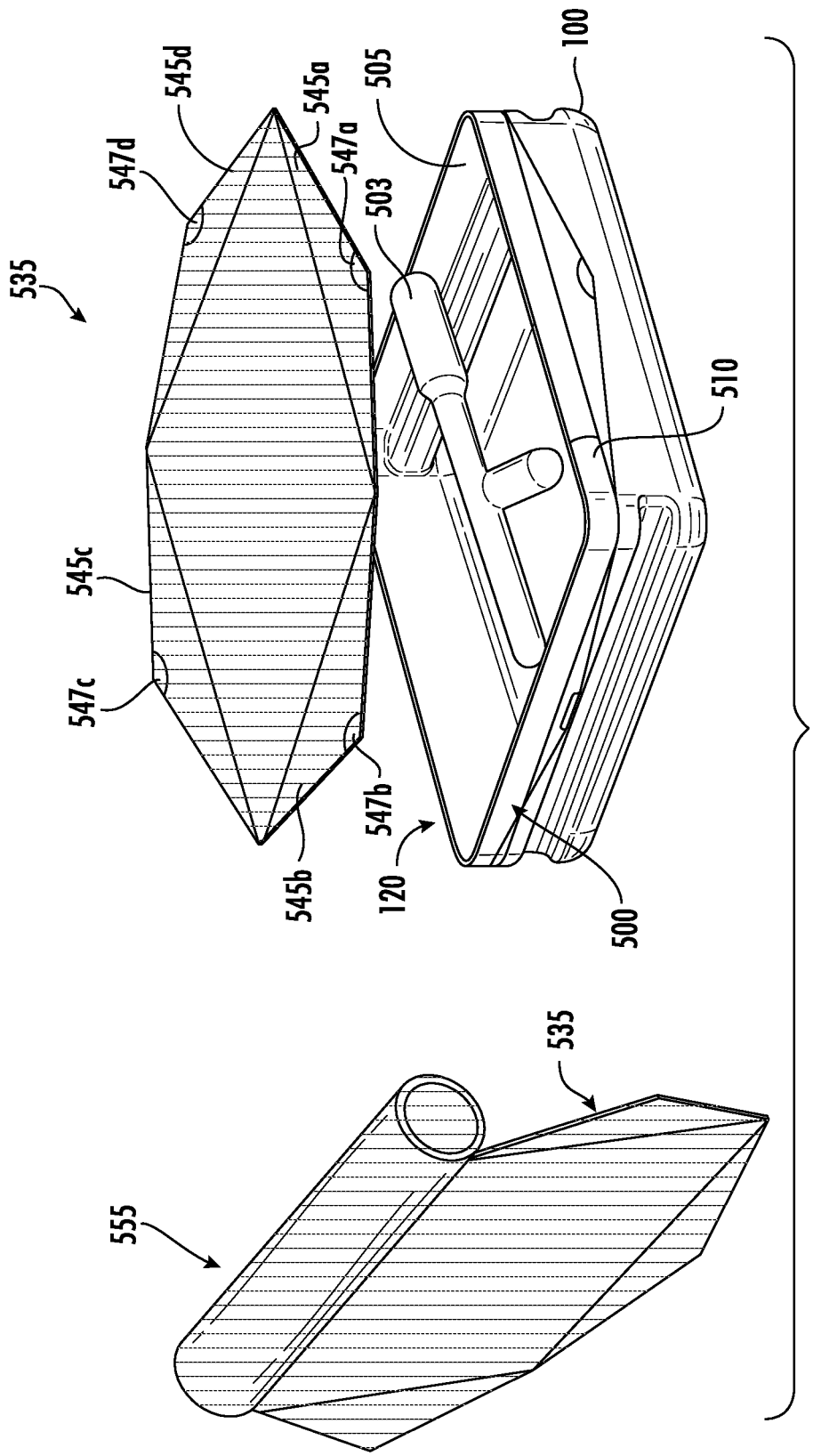

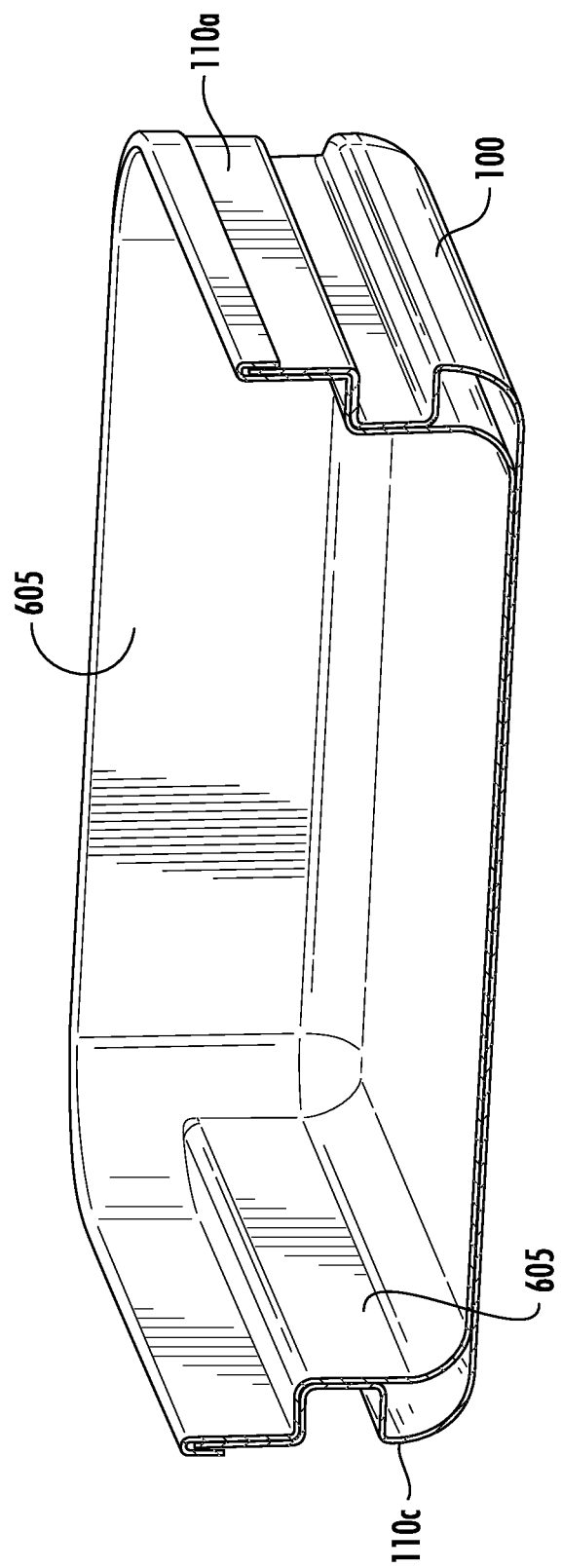

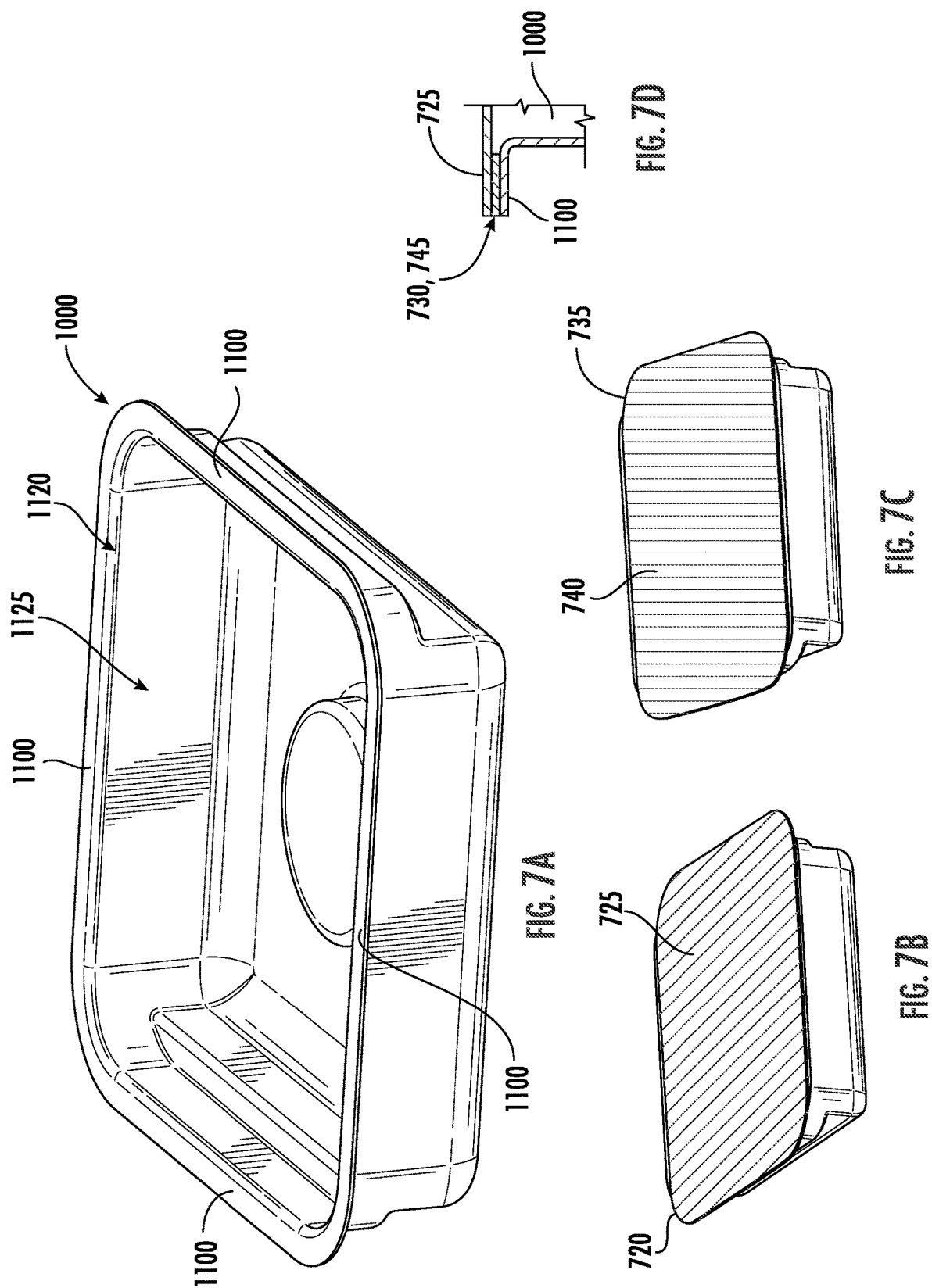

MEDICAL DEVICE TRANSPORTATION SYSTEMS

CROSS REFERENCE TO RELATED APPLICATIONS

The present application is a non-provisional of, and claims the benefit of priority under 35 U.S.C. § 119 to, U.S. Provisional Application Ser. No. 62/953,352, filed Dec. 24, 2019, the disclosures of which are herein incorporated herein by reference in their entirety.

FIELD

The present disclosure relates generally to containment and transportation systems, and more particularly, containers and methods for transporting medical devices.

BACKGROUND

Some devices, including endoscopes, may be reusable for on-going patient use. Medical facilities, such as clinics or hospitals, may manually clean and high-level disinfect each device between use, and may need to transport the devices from a reprocessing or storage location to another location for use in a medical procedure. Clean medical devices may be deliverable to the medical professional for performing a medical procedure and used medical devices may be deliverable to the reprocessing or storage location.

One challenge for medical facilities is to maintain a workflow of the clean and used medical devices to minimize cross-contamination and a potential spread of infections and/or diseases. Current medical device containment and transportation systems used in medical facilities may be difficult to clean, e.g., including configurations that may allow for bacteria and other contaminants to remain on the surfaces even after disinfecting processes. Clean medical devices may be at risk of contamination in the event the containment systems are not thoroughly disinfected.

Additionally, existing containment and transportation systems may only be used exclusively together, so that medical facilities may be limited to a particular container to be used with a transportation system. Thus, medical facilities may be unable to swap out particular container configurations in different types of transportation systems as desired.

It is with respect to these and other considerations that the present improvements may be useful.

SUMMARY

This Summary is provided to introduce a selection of concepts in a simplified form that are further described below in the Detailed Description. This Summary is not intended to necessarily identify key features or essential features of the claimed subject matter, nor is it intended as an aid in determining the scope of the claimed subject matter.

A system is disclosed for containing and transporting a medical device. The system may include a container including a bottom face and surrounding side faces as a closed first end and an open second end to form an inner portion for receiving and retaining the medical device. The system may also include a liner removably attachable to the container, the liner extendable over a portion of the side faces to line the inner portion of the container. A cover may be removably attachable to the container, the cover extendable over the liner and the container to encapsulate a medical device placed on the liner within the container. The cover may be attachable to the container via a tab. The liner may be coupleable to one of the side faces by an adhesive pull-tab. The cover may be coupleable to one of the side faces or the liner by an adhesive pull-tab.

The system may also include a first cover removably attachable to the liner and extendable across the open second end of the container to enclose the inner portion, and a second cover removably attachable to the first cover and extendable over at least a portion of the side faces and across the open second end of the container to enclose the inner portion. The first cover may be exchangeable with the second cover for visual verification of a condition of the medical device. The first and second covers may be coupled to the liner along an edge of the liner. The first cover may be perforated at or near a location of its attachment to the second cover so that the first cover is removable from the second cover. The first cover may be positionable over the second cover so that when the first cover is in a closed position with respect to the container the second cover is covered by the first cover.

A first cover may be removably attachable to at least one of the liner and the side face of the container, and may be extendable across the open second end of the container to enclose the inner portion. The first cover may be removably attachable to at least one of the liner and the side face of the container, and extendable across the open second end of the container to enclose the inner portion; the first may be is exchangeable with the second cover for visual verification of a condition of the medical device.

The first cover may comprise a cover portion and a plurality of extensions that are extendable beyond edges of the cover portion so that when the first cover is placed over the second open end of the container, the extension portions extend over the side faces of the container. The second cover may comprise a cover portion and a plurality of extensions that are extendable beyond edges of the cover portion so that when the second cover is placed over the second open end of the container, the extension portions extend over the side faces of the container.

Each of the extensions of the first and second cover portions may include an adhesive region on a container-facing side thereof. The adhesive regions may allow the user to press the extension portions against an associated side of the container to fix the extension portions to the side of the container to maintain the first or second cover in place over the second open end of the container. The first cover portion may be dispensable from a rolled tube containing a plurality of said first cover portions, and the second cover portion is dispensable from a rolled tube containing a plurality of said second cover portions. The liner may be formed from a flexible thermoformed material that closely conforms to surfaces forming the inner portion of the container.

The container and the liner may be a single integral piece. The container may include a laterally extending ledge portion disposed about a perimeter of the second open end of the container, the ledge portion providing a flat surface for receiving the cover. The cover may include a closure feature comprising an adhesive disposed on a container-facing side of cover, the adhesive enabling a user to press the cover against the laterally extending ledge portion of the container to fix the cover to the container, thus maintaining the cover coupled to the container.

A system is disclosed for containing and transporting a medical device. The system may include a container including a bottom face and surrounding side faces as a closed first end and an open second end to form an inner portion for receiving and retaining the medical device. The system may also include a liner removably attachable to the container to line the inner portion of the container. The system may further include a cover removably attachable to the container via a tab to encapsulate a medical device placed on the liner within the container.

At least one of the liner and the cover may be coupleable to one of the side faces by an adhesive pull-tab. The system may further include a first cover extendable across the open second end of the container to enclose the inner portion, and a second cover removably attachable to the first cover and extendable across the open second end of the container to enclose the inner portion. The first cover may exchangeable with the second cover for visual verification of a condition of the medical device.

The first cover may include a cover portion and a plurality of extensions that are extendable beyond edges of the cover portion so that when the first cover is placed over the second open end of the container, the extension portions extend over the side faces of the container. The second cover may include a cover portion and a plurality of extensions that are extendable beyond edges of the cover portion so that when the second cover is placed over the second open end of the container, the extension portions extend over the side faces of the container. The first cover may have a first color or first marking indicating the medical device is clean, while a second cover may have a second color or marking indicating the medical device is used.

The liner may be formed from a flexible thermoformed material. The container and the liner may be single integral piece. The container may include a laterally extending ledge portion providing a flat surface for receiving the cover, and the cover includes a closure feature comprising an adhesive disposed on a container-facing side of cover, the adhesive enabling a user to press the cover against the laterally extending ledge portion of the container to fix the cover to the container, thus maintaining the cover coupled to the container.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures:

FIGS. 1A-1I illustrate an exemplary embodiment of a container in accordance with the present disclosure.

FIG. 2A illustrates partial view of an exemplary embodiment of a containment and transportation system in accordance with the present disclosure;

FIG. 2B illustrates a cross-sectional view of an exemplary embodiment of a plurality of containers in a stacked configuration in accordance with the present disclosure;

FIGS. 2C-2D illustrate exemplary embodiments of a containment system in accordance with the present disclosure;

FIGS. 3A-3F illustrate an exemplary embodiment of a container, liner and lid arrangement in accordance with the present disclosure;

FIGS. 4A-4C illustrate an exemplary embodiment of a container, liner and lid arrangement in accordance with the present disclosure;

FIGS. 5A-5D illustrate an exemplary embodiment of a container, liner and lid arrangement in accordance with the present disclosure;

FIGS. 6A-6D illustrate an exemplary embodiment of a container, liner and lid arrangement in accordance with the present disclosure;

FIGS. 7A-7D illustrate an exemplary embodiment of a container, liner and lid arrangement in accordance with the present disclosure.

DETAILED DESCRIPTION

Figure 1C:
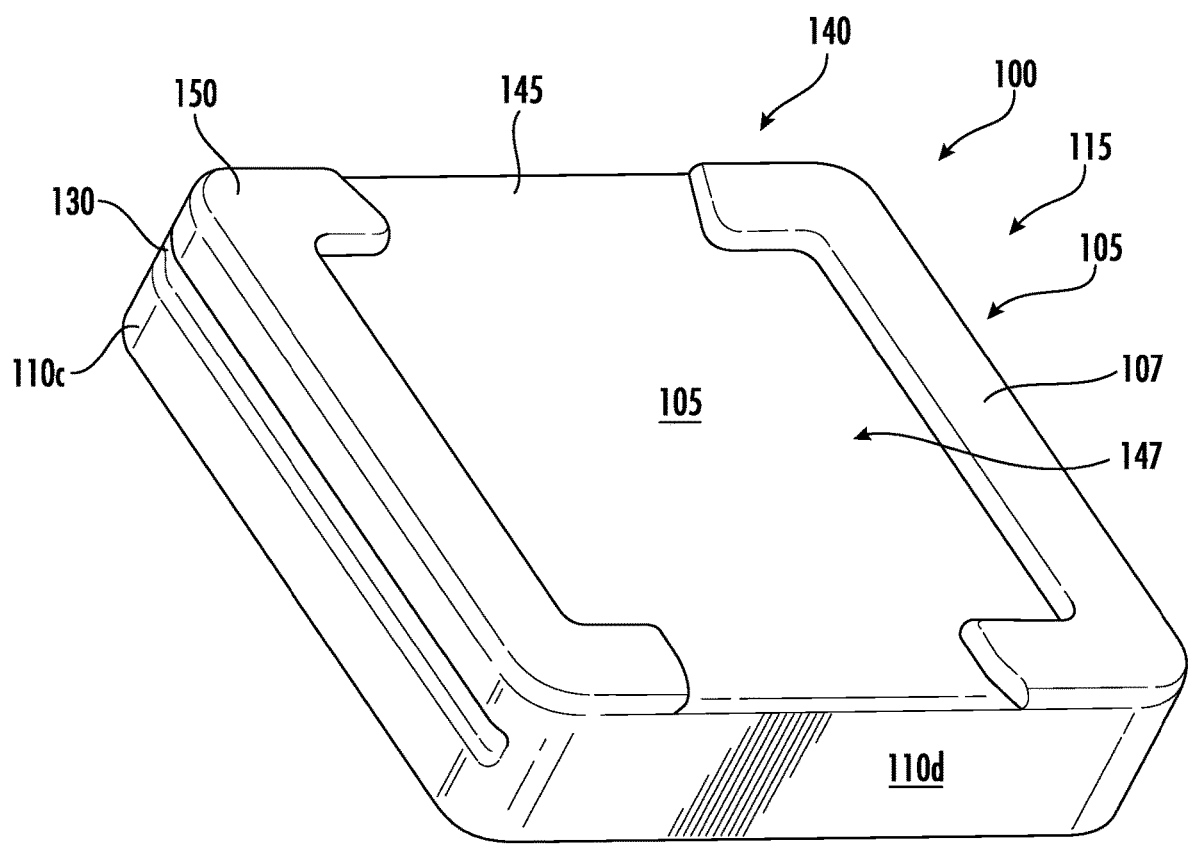

The present disclosure is not limited to the particular embodiments described herein. The terminology used herein is for the purpose of describing particular embodiments only and is not intended to be limiting beyond the scope of the appended claims. Unless otherwise defined, all technical terms used herein have the same meaning as commonly understood by one of ordinary skill in the art to which the disclosure belongs.

As used herein, the singular forms "a," "an," and "the" are intended to include the plural forms as well, unless the context clearly indicates otherwise. It will be further understood that the terms "comprises" and/or "comprising," or "includes" and/or "including" when used herein, specify the presence of stated features, regions, steps elements and/or components, but do not preclude the presence or addition of one or more other features, regions, integers, steps, operations, elements, components and/or groups thereof.

Exemplary embodiments of containment and transportation systems and methods according to the present disclosure may be configured for improved cleanability or disinfection, to reduce a risk of contamination of medical devices. Exemplary embodiments may also be configured to minimize or prevent inadvertent re-use of a device that has not been reprocessed, and/or inadvertently reprocessing an already reprocessed device that is thought to have been used. As described above, existing systems may be configured with features such as undercuts, lips, notches, or the like, that may trap contaminants. During handling, a medical professional may contact the contaminated undercut or lip, potentially transferring contaminants to a clean medical device and thereby increasing a risk of spreading diseases to a patient.

A containment system in accordance with the present disclosure may include a container having an improved design to minimize contamination for receiving, handling and retaining a medical device, which may be transported throughout a medical facility for reprocessing and patient use. Referring now to FIGS. 1A-1G, an exemplary embodiment of a container 100 is depicted. The container 100 may be formed as a tray, or basket, or a shallower type of receptacle, for receiving and retaining a medical device. The container 100 may have a bottom face 105, and surrounding side faces 110a-110d, to form the container having a closed first end 115 and an open second end 120. The open-ended container 100 may have an inner portion 125 formed by the bottom face 105 and surrounding side faces 110a-110d, e.g., such that a medical device is receivable by placement on the bottom face 105 and retainable inside the container by the surrounding side faces 110a-110d. In some embodiments, the side faces 110a-110d may extend along a straight line that is vertical to the bottom face 105 (e.g., FIGS. 1A-1C), and in other embodiments one or more of side faces 110a-

110d may extend along a straight line that tapers inward from the open second end 120 to the closed first end 115. For example, referring to FIGS. 1D-1I, the container 100 may include vertical sides faces 110b, 110d along the front and back of the container, while side faces 110a, 110c along the sides of the container including indentations 130 may taper slightly inward from vertical extending from the open second end 120 to the closed first end 115. FIG. 1E depicts a taper of $\theta_{SW}$ degrees from vertical that may be a range of 0 degrees to about five degrees. The taper may help to provide clearance between side surfaces 110a, 110c of the container and the sides of a transportation device when the container is loaded in the device. Alternatively, or additionally, the taper may help in the manufacturing process for the container, e.g., to aid in releasing the container from an injection mold if that forming technique is used.

In some embodiments, the container 100 may be formed as a rectangle, or square, e.g., having four side faces 110a-110d, although it is envisioned that the container may be formed with any number "n" of side faces. Additionally, the container 100 may have rounded edges 107 connecting the bottom face and surrounding side faces, which may be advantageous for a more thorough disinfection as well as handling. In embodiments with a tapered side face, the side face may be made to follow a straight line from the open second end to the closed first end and tangential to the apex of the rounded edge 107 (see FIG. 1E). The container may be formed of a substantially rigid material, such as a plastic or composite, and may be thermoformed or molded as a single piece to its configuration.

The container 100 may have one or more indentations 130. In embodiments, a first indentation 130a may extend along at least a portion of a first side face 110a, e.g., substantially parallel to the bottom face 105. Similarly, a second indentation 130a may extend along at least a portion of a third side face 110c, e.g., substantially parallel to the bottom face 105 and in alignment with the first indentation 130a. The indentations may extend along the full length of the respective face, although in some embodiments the indentations may extend along a portion of the side face. In some embodiments, the container 100 may have two indentations 130a, 130b, along opposing side faces, to be received by a transportation device. Indentations may also be included in at least a portion of the other side faces 110b, 110d, etc. The indentations 130 may be substantially symmetrical to each other, e.g., so that the container 100 may be receivable into a transportation device in an upright position. In embodiments, the container may be receivable into a cart, for transport in a medical facility.

The indentations 130 may be formed to extend inward into the inner portion 125. In some embodiments, the indentations 130 may be formed as rails, e.g., having a rectangular cross-section. The indentations may be formed inward so that a user, e.g., a medical professional, may grip the container 100 by the indentations 130 (e.g., surfaces 135a). The medical professional may alternatively and/or additionally handle the container 100 via the bottom face 105 and/or side faces 110a-110d (e.g., rounded edges 107). In embodiments, the medical professional may slide a container 100 in and out of a transportation device, such as a cart, and may carry the container 100 to a reprocessing location and/or a patient procedure location. The indentations 130 may have surfaces 135a-135c formed substantially perpendicular to each other (90 degrees±10 degrees), although in some embodiments one or more of the surfaces may form an obtuse angle (≥90 degrees). The surfaces 135a-135c of the indentations 130 may be cleanable, e.g., contaminants may not be trapped in the indentations, so that when the medical professional grips and carries the container 100 as needed, cross-contamination may be minimized. In embodiments, corners of the surfaces 135a-135c may have radii to enhance cleanability of the container 100, which may be dimensioned between approximately 0.100 to 0.180 inches for cleaning. The surfaces 135a-135c may be a "C" or "U" shape, to create an opening "o". As described below, the opening "o" may be sized as desired, e.g., to allow for handling by a medical professional and/or for receiving a cover, a liner, or both, e.g., based on the surface 135b formed substantially perpendicular relative to the bottom face 105.

In some embodiments, the indentations 130 may have a uniform height of opening along the side face (e.g., FIG. 1C), and in other embodiments the indentations may have a height of opening that increases at one or both ends of the indentation. Referring to FIG. 1F, container 100 includes indentations 130 extending along the side faces 110a, 110c, with flared end openings 132. The height of the middle length of indentation 130 is represented as $d_{CI}$ and the height of the flared end openings 132 is represented as $d_{TI}$ Height $d_{TI}$, may gradually decease to height $d_{CI}$, through the length of the flare end openings 132. For example, at a maximum height, flared end openings 132 may be approximately 30%-50% greater than the height of the middle length of indentations 130. Flare end openings may assist with aligning the opening of indentation 130 with the rails 215 of a transportation device 505a, 505c, as the container is loaded into the device. Flare end openings 132 may also provide some gap clearance between the edges of the opening of indentation 130 and the edges of rails 215 to facilitate sliding the container into a transportation device along the rails. In some embodiments, one or both ends of indentations 130, whether flared or not, may include a portion 135d that wraps around from the side face with the indentation to the adjacent side face (see, e.g., FIG. 1D). This may assist with alignment and starting the indentation along the rails of a transportation device once aligned.

In embodiments, the indentations 130 may be formed to allow for the container 100 to be compatibly receivable into a plurality of transportation devices. For example, the container 100 may be receivable in a first transportation device, and a second transportation device, where the first and second transportation devices have differing configurations. It is understood that the container may be compatibly receivable in any number "n" of transportation devices of differing configurations. The indentations may extend inwardly into the inner portion 125 a depth such that the container is adaptably receivable into carts having different configurations. In some embodiments, the container 100 and the indentations 130 may be dimensioned to be receivable in the transportation devices. In this matter, the container 100 may be compatible with a variety of transportation systems (see FIGS. 2A-2D).

Additional features may also include contouring and/or beveling on the rounded edges 107 at the corners of the container 100 underneath the indentations 130, as described in more detail in U.S. Nonprovisional Patent Application titled "Medical Device Containment and Transportation Systems and Methods," filed Dec. 24, 2019, and U.S. Provisional Patent Application titled "Medical Device Transportation Systems," filed Dec. 24, 2019, the entirety of which applications are incorporated by reference herein.

The bottom face 105 of the container 100 may include a contour 140. The contour 140 may include recessed portions 145, e.g., an outer surface 148 of the bottom face 105 may be disposed inward from portions 150 of the bottom face 105. The recessed portions 145 may be positioned substantially along the side faces 110b, 110d opposite of side faces having the indentations 130a, 130b, and/or along a central portion 147 of the bottom face 105. In some embodiments, side faces 110a, 110c may have at least the portions 150.

Figure 1D:
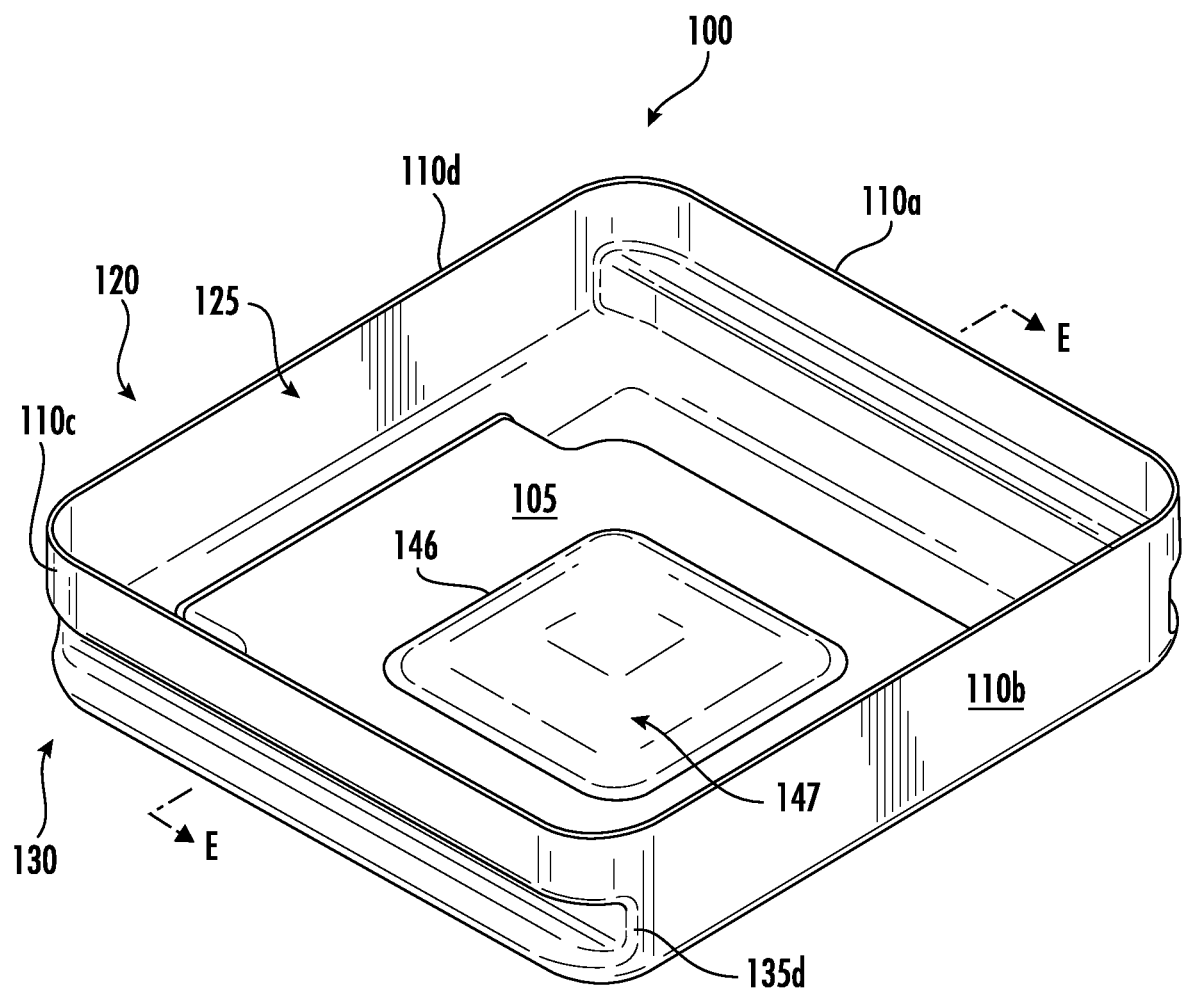
Figure 1E:
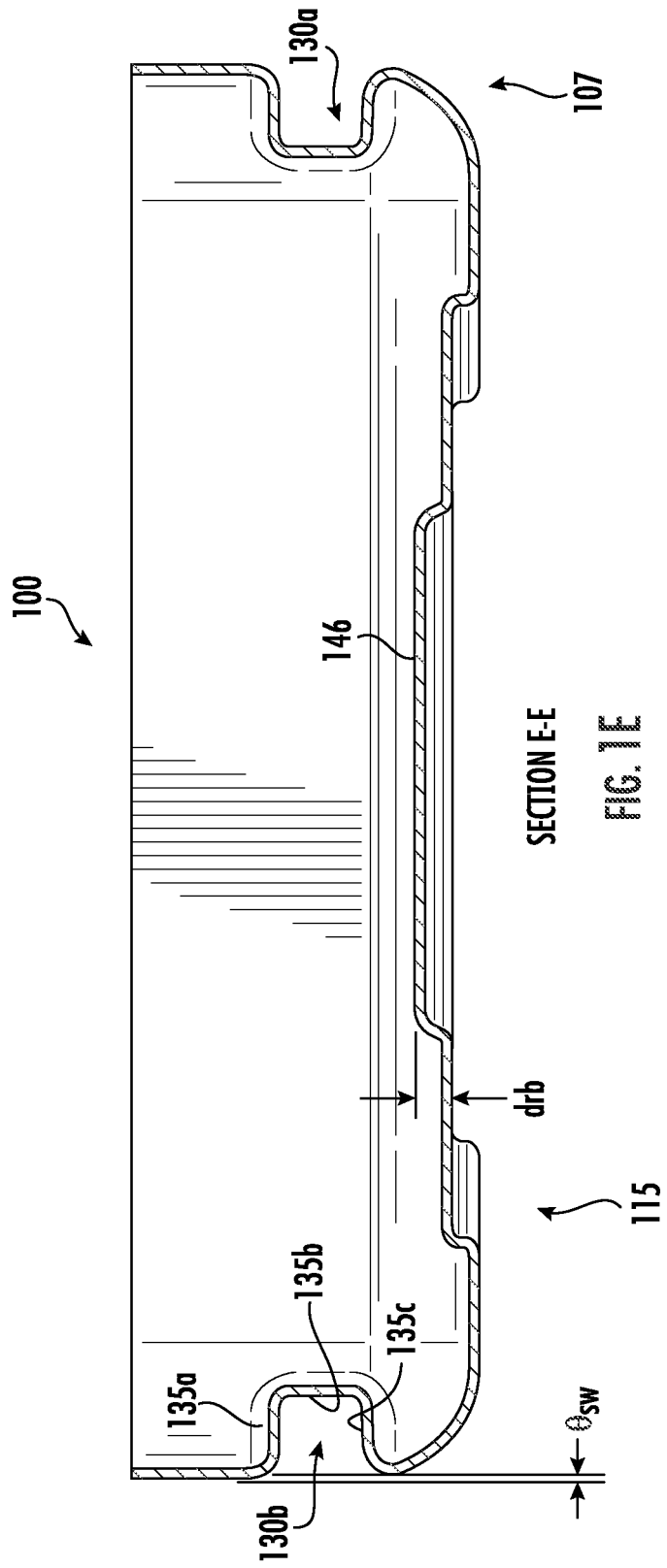
Figure 1F:
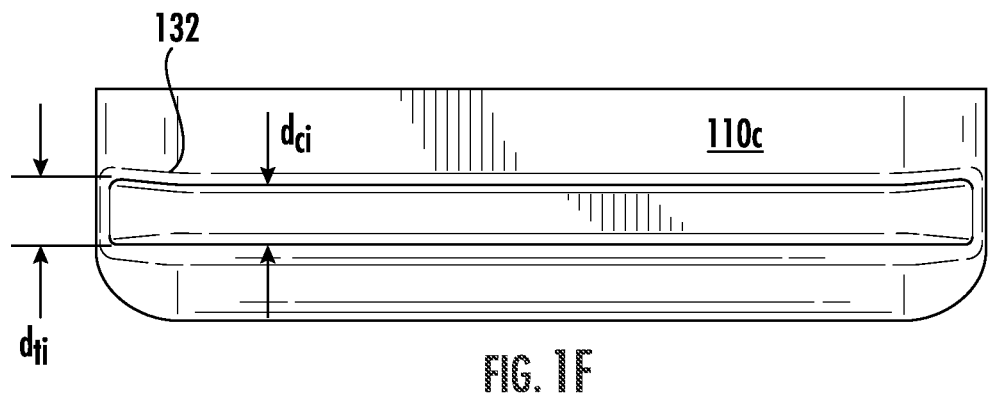
Figure 1G:
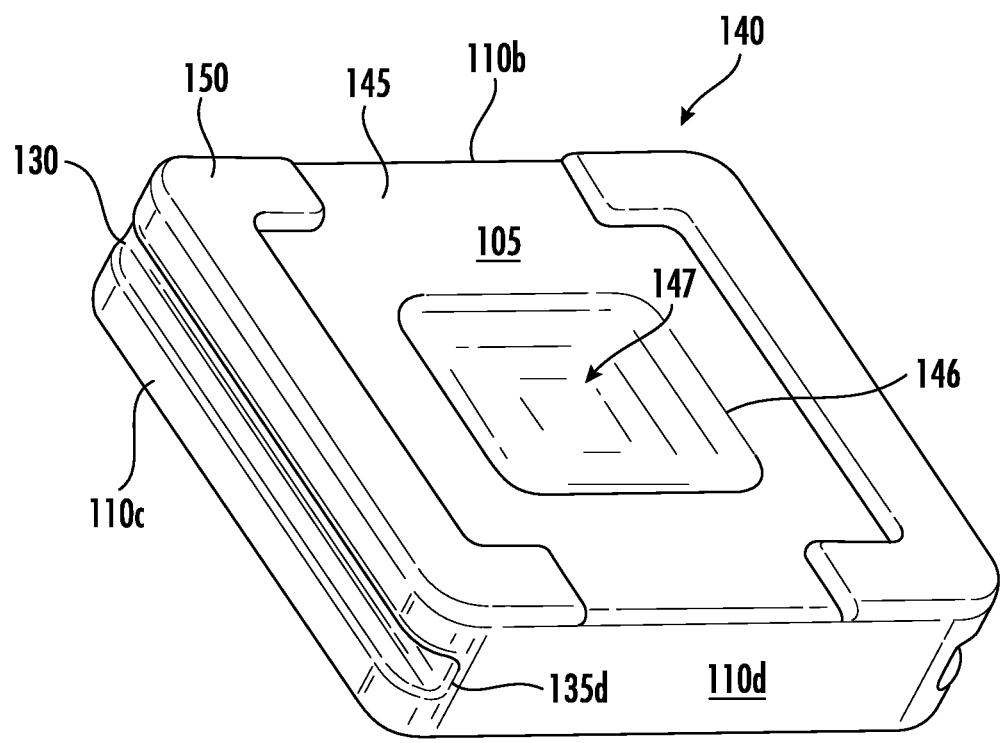

In some embodiments, the central portion 147 of the bottom face 105 may include an indentation 146 that extends from the surface of the recessed portion 145 of the bottom face 105 into the inner portion 125 (e.g., FIGS. 1D-1H). Referring to FIGS. 1D-1E, indentation 146 may have a square shape and extend into inner portion 125 a distance $d_{RB}$ that may range from about 0 mm. to about 25 mm. As shown, indentation 146 may extend into inner portion 125 a distance $d_{RB}$ of 0.4 in. (10.16 mm). The shape of indentation 146 is depicted as a square, but may be any number of other shapes, such as circular, oval, rectangular, etc. The profile of the indentation 146 may have a plateau-like cross-section, as shown, with a step-up around the edges and a relatively flat portion parallel to the bottom face 105 and recessed portions 145. Alternatively, indentation 146 may have a dome-like cross-section, with a gradual slope from recessed portion 145 of bottom face 105 to an apex at central portion 147, and then a gradual slope back to recessed portion 145.

The bottom face 105 and recessed portions 145 may allow for the container 100 to be received in a transportation device in a plurality of orientations. As shown in FIG. 2C, a first container 200a may be receivable into a transportation device 205c via the indentations 130 in a first orientation. The transportation device 205c may be configured such that a container may not be receivable in a lower portion 205 in the first orientation. In some embodiments, the transportation device 205c may lack means for receiving a container by the indentations 130, and/or include additional elements that may otherwise prevent the first container 200a from being received, e.g., support elements at a bottom portion of the transportation device 205c. In this event, a second container 200b may be receivable into the transportation device 205c in a second orientation, e.g., rotation of the container 90° about a central axis 155. The recessed portion 145 may allow for the second container 200b to fit in the transportation device 205c with enough vertical clearance from an above first container 200a. In some embodiments, the container 100 may be formed in a rectangle, so that in the second orientation the second container 200b is receivable in a narrower configuration than in the first orientation. It is understood that the first and second containers 200a, 200b may include the features described with respect to the container 100.

Figure 1H:
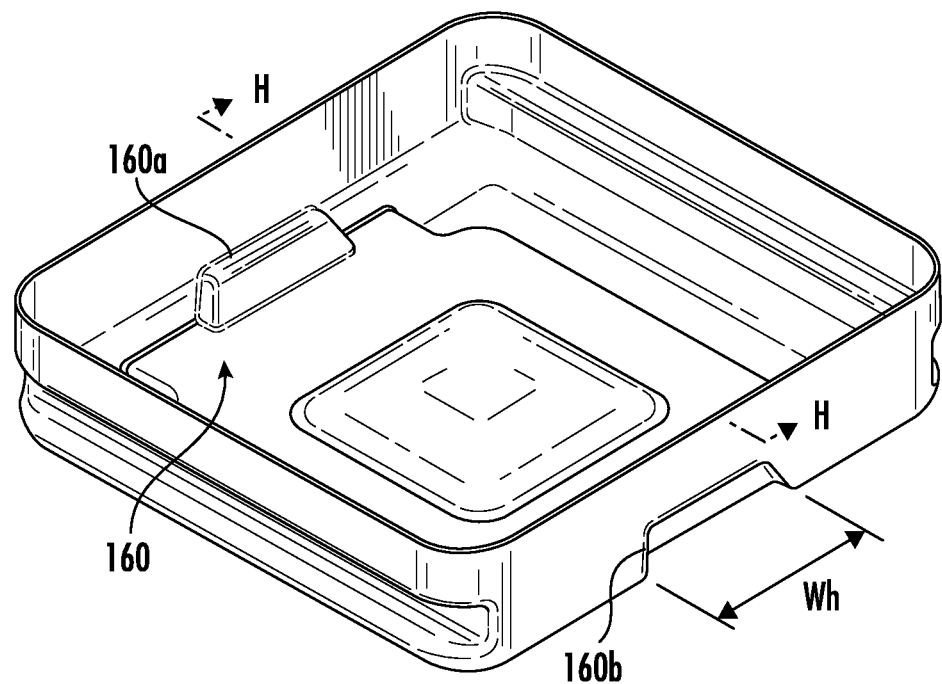
Figure 1I:
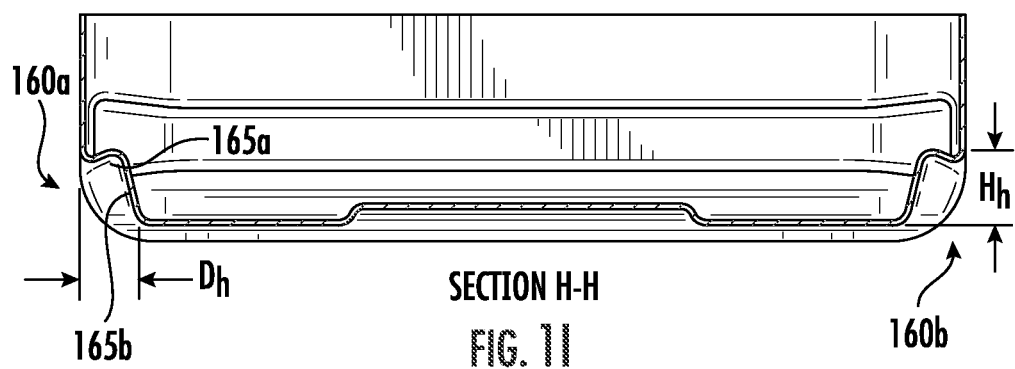
Figure 2D:
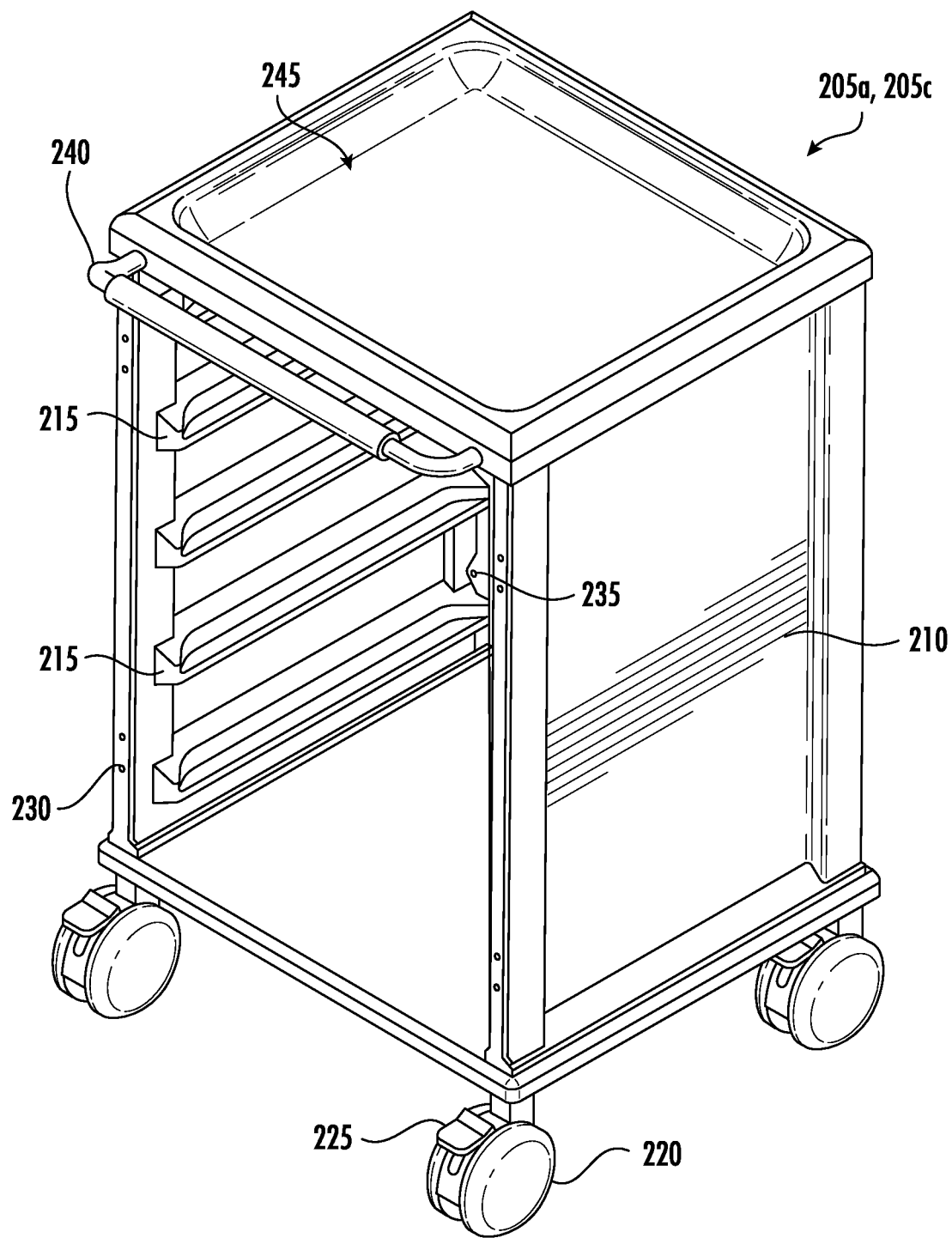

In some embodiments, the bottom face 105 and/or surrounding side faces 110a-110d, may incorporate a handle 160, 170, 180 to facilitate holding and movement of the container 100 (see FIGS. 1H-1I). Referring to FIGS. 1H-1I, a container 100 with corner handles 160 is depicted. Respective corner handles 160a, 160b may be integrated into opposite sides faces 110b, 110d, and their adjoining recessed portions 145 of bottom face 105. Each handle 160a, 160b, may have a width $W_h$, height $H_h$ and depth $D_h$ dimension that is sized to accommodate the fingers of a user's hand grasping the container palm-side upward. For example, each handle 160a, 160b, may have a width $W_h$ that extends 3-7 in. (76.2-177.8 mm), height $H_h$ that extends 1.0-3.0 in. (25.4-76.2 mm), and depth $D_h$ that extends 0.5-2.0 in. (12.7-50.8 mm). Handles 160a, 160b, may extend inward from respective side faces 110b, 110d into the inner portion 125 of the container 100, and may include a sloped vertical face 165b that transitions to a recessed dimple 165a. Dimple 165a may be sized to accommodate a user's fingertips when grasping the container 100. Other shapes and dimensions of handles 160, 170, 180 may be possible depending on user requirements. Handles 160, 170, 180 may provide a more secure grasping feature compared to holding a container from the bottom face 105 and/or side faces 110a-110d, particularly if the container is encased in a liner (e.g., liner 300, FIG. 3A). For example, the handle 160a, 160b may not extend along an entire length of a side face 110a-110d.

As shown in FIG. 2B, a first container 200a may be configured to be stacked with a second container 200b, by nesting an optional lid 202 disposed on an upper surface of the second container 200b with the bottom face 105 of the first container. The first and second containers 200a, 200b may include the features described above with respect to container 100 described in relation to FIGS. 1A-1I and may be removably attachable to a respective optional lid 202. The nested configuration may allow for the containers to be stacked, e.g., vertically stacked, relative to each other, which may be advantageous for storing extra containers in a medical facility, and/or during transport of a plurality of containers. For example, the nesting configuration may provide stability to the stack of containers to reduce a likelihood of tipping over, which may reduce potential contamination of a medical device. The lid 202 may be formed of a substantially rigid material such as a plastic or composite material and may be a single piece thermoformed or molded configuration.

The containment and transportation system may further include a liner for lining the inner portion 125 of the container 100. In embodiments, a liner may be included so that when a medical device is placed in the inner portion 125 of the container 100, the liner may act as a protective barrier to the inner portion 125. This may aid in minimizing potential contamination of the container, e.g., when receiving and/or retaining a used medical device. When the medical device is removed for cleaning, the liner may be disposed of so that the container may avoid direct contact with the used medical device. In some embodiments the containment and transportation system can include a cover. As will be described in greater detail later, the cover may be extendable across the second open end 120 of the container 100, so that a medical device placed in the inner portion 125 of the container is enclosed between the liner and the cover.

Referring now to FIGS. 3A-3F, an embodiment of a liner and cover arrangement will be described in greater detail. The liner 300 may have a lining portion 305 and a closure feature 310. The lining portion 305 may be sized to extend over the side faces 110a-110d of the container 100 and line the inner portion 125 (FIG. 1A). The lining portion 305 may be extendable fully over at least a portion of the side faces 110a-110d of the container 100. The lining portion 305 partially or substantially enclose the container 100 to act as a protective barrier and prevent and/or minimize direct contact between a medical device and the container, and/or between a user and the medical device and/or container. The lining portion 305 may be formed of a flexible material, such as a single plastic sheet, and may have a closure feature 310 that may secure the liner 300 to the container 100. The flexible material may allow for the liner 300 to be conformable to a profile of the container 100, e.g., the liner may surround the side faces 110a-110d and may sit in the inner portion 125 of the container (FIG. 1A). In embodiments, the liner 300 may be at least partially substantially transparent or translucent, although it is also envisioned that the liner 300 may be colored, or opaque.

The liner 300 may be removably attachable to the container by the closure feature 310, so that when the container 100 is lined, the closure feature 310 maintains the liner 300 in position with respect to the container 100. By aligning the liner 300 so that the lining portion 305 is continuously extended across the inner portion 125 of the container 100, contamination of the container may be minimized.

In embodiments, the closure feature 310 may be a pull-tab 315 that can be removably fixed to a surface of the container 100 once the liner 300 has been cinched around the side faces 110a-110d of the container. The liner 300 may be placed over the container 100 with the pull-tab in an un-extended position. Once the liner 300 is positioned to enclose the container 100, the pull-tab 315 may be moved to an extended position, thereby cinching the liner 300 around the side faces 110a-110d of the container. An adhesive may be provided on a container-facing side of the pull-tab 315. This adhesive may allow the user to press the pull-tab 315 against the associated side 110a-110d of the container 100 to fix the pull-tab 315 to the side of the container, thus maintaining the liner 300 cinched around the container. In some embodiments the liner 300 may be configured so that the adhesive applied to the pull-tab 315 fixes the pull-tab to another portion of the liner, thus maintaining the liner cinched around the container 100. In some embodiments the adhesive may allow the pull-tab 315 to be removably fixed to the side faces 110a-110d of the container 100 or another portion of the liner 300 so that the pull-tab 315 can be released from the side of the container or another portion of the liner to release the liner from the container after use. The pull-tab 315 may, in some embodiments, be elastic so that it is at least partially extensible when configured in the extended state.

Although a pull-tab closure is illustrated in FIGS. 3A-3F, it will be understood that the liner 300 may be removably attachable to the container 100 in any manner, including but not limited to an elastic, a drawstring, an adhesive, hook-and-loop fasteners, or the like.

As mentioned, the liner 300 may be extendable partially over the side faces 110a-110d, so that the closure feature 310 remains in a stretched position around the side faces 110a-110d. FIGS. 3D-3F show three example configurations in which the liner 300 extends over different portions of the side faces 110a-110d of the container 100. In FIG. 3D, the liner 300 extends over only a top portion of the side faces 110a-110d; in FIG. 3E, the liner extends over an upper half portion of the side faces, and in FIG. 3F, the liner extends over substantially the entirety of the side faces.

As described, the liner 300 may be removably attachable to the container 100 prior to placement of medical device (not shown) in the inner portion 125 of the container. As will be appreciated, a medical device may be placed in an inner portion 125 of a container 100 (FIG. 1A) after the liner 300 is attached to the container. When the medical device is placed in the container 100, at least one cover may be extendable across the second open end 120, so that the medical device is captured between the liner 300 and the cover. Referring to FIGS. 3B and 3C, a first cover 320 may have a cover portion 325 and a closure feature 330, and a second cover 335 may have a cover portion 340 and a closure feature 345. In embodiments, the covers 320, 335 may be formed of a flexible material, such as a single plastic sheet having a closure feature 330, 345 to an edge thereof. The flexible material may allow for the first and second cover 320, 335 to extend across the container 100, e.g., the first and/or second cover 320, 335 may form a barrier across the second open end 120 of the container 100. In embodiments, the first and/or second cover 320, 335 may be at least partially substantially transparent or translucent. It is also envisioned that the first and second covers 320, 335 may be different colors, and/or may include symbols, patterns and/or words to indicate the status of the medical device. Different colors and/or patterns may provide an easy indicator for medical professionals traversing through a medical facility, picking up used medical devices and/or delivering clean medical devices, so that incorrect delivery of a medical device is minimized. In embodiments, the liner 300, first cover 320 and/or second cover 335 may include a section for writing on the top surface. Details regarding the medical device may be included by a medical profession, e.g., to document details such as the time the medical device was used, to track a time from use to cleaning. In some medical facilities, a used medical device must be reprocessed within a predetermined time period, such as less than 1 hour. In some embodiments, the first cover 320 may be different than the second cover 335, so that a medical professional may have a visual indication of a condition of the medical device in the container 100. For example, a green colored cover 320 may indicate a clean medical device. A medical professional may be able see the green cover 320 and transport the medical device to a patient procedure location for use. Similarly, a red colored cover 335 may indicate a used medical device, so the medical professional may transport the medical device to a reprocessing location. In some embodiments, a hazardous waste symbol, and/or a pattern of hazardous waste symbols, may be printed on a cover 320, 335 to indicate a used medical device, so that the pattern may indicate to a medical professional for proper handling and disposal. Symbols or other printing may be printed on each side of the cover, with each side being different colors. For example, symbols may be printed in green on a first side of the cover and red on a second side of the cover, so that a single cover may be used in the system.

The first and/or second covers 320, 335 may be removably attachable to the container by the respective closure feature 330, 345, so that the covers 320, 335 are substantially taut (e.g., the covers may not sag into the inner portion 125 of the container) across the second open end 120. The first and/or second covers 320, 335 may be exchangeable with each other, e.g., by the medical professional. For example, after endoscope reprocessing, a clean medical device may be placed in a lined container, and a first cover 320 may be extended across the second open end 120, which may be green in color. The container may be transported from a reprocessing location to a medical procedure location, where the clean medical device may be used on a patient. Subsequent to the procedure, the used medical device may be placed back in the container, and a second cover 335 may be extended across the second open end 120, which may be red in color. This may indicate to a medical professional, or other medical facility personnel that the medical device should be transported back to the reprocessing area for cleaning.

Similar to the liner 300, the first and/or second cover 320, 335 may enclose a portion of the side faces 110a-110d of the container 100 (FIG. 1A), as well as a portion of the already-attached liner 300. By aligning the first and second covers 320, 335 so that the cover portions 325, 340 may be continuously extended across the inner portion 125 of the container 100, a clean medical device may be protected from outside contamination. Additionally, a used medical device, which may include contaminants from a patient, may be containable by the first or second cover 320, 335, and the liner 300.

In embodiments, the first and second covers 320, 335 may be removably attachable to the container 100 by respective closure features 330, 345, so that when the container 100 is covered, the associated closure features 330, 345 maintain the covers 320, 335 in position with respect to the container 100. In embodiments, the closure features 330, 345 can be pull-tabs 332, 347 that can be removably fixed to a surface of the container 100 once the respective cover 320, 335 has been cinched around the side faces 110a-110d (FIG. 1A) of the container. The selected cover 320, 335 may be placed over the container 100 with the pull-tabs 332, 347 in an un-extended position. Once the cover 320, 335 is positioned to enclose the container 100, the pull-tab 332, 347 may be moved to an extended position, thereby cinching the cover 320, 335 around the side faces 110a-110d of the container.

In some embodiments, an adhesive may be provided on a container-facing side of each pull-tab 332, 347. This adhesive may allow the user to press the pull-tab 332, 347 against the associated side 110a-110d of the container 100 to fix the pull-tab 332, 347 to the side of the container, thus maintaining the cover 320, 335 cinched around the container. In some embodiments the cover 320, 335 may be configured so that the adhesive applied to the pull-tab 332, 347 fixes the pull-tab to a portion of the liner 300, thus maintaining the cover 320, 335 cinched around the container 100. In some embodiments the adhesive may allow the pull-tab 332, 347 to be removably fixed to the side faces 110a-110d of the container 100 or a portion of the liner 300 so that the pull-tab 332, 347 can be released from the side of the container or the liner to release the cover 320, 335 from the container after use. The pull-tab 332, 347 may, in some embodiments, be elastic so that it is at least partially extensible when configured in the extended state. Although a pull-tab closure is illustrated in FIGS. 3B-3C, it will be understood that the cover 320, 335 may be removably attachable to the container 100 in any manner, including but not limited to an elastic, a drawstring, an adhesive, hook-and-loop fasteners, or the like.

In some embodiments, the first and/or second cover 320, 335 can be form fitting to the shape of the container 100 so that when the first and/or second cover 320, 335 is fit over the container, the cover(s) fit snugly to the side faces 110a-110d of the container 100 (FIG. 1A) even before the respective pull-tab 332, 347 is extended and fixed to one of the side faces of the container or the liner 300. In other embodiments, the first and/or second cover 320, 335 is slightly oversized or is bag-shaped so that it can be easily placed over the container 100 to provisionally cover the container. In such embodiments, the pull-tab 332, 347 may be extended and adhered to the side of the container 100 or the liner 300 to cinch the cover 320, 335 to the container.

Referring now to FIGS. 4A-4C, an embodiment of a liner and cover arrangement will be described in greater detail. The liner 400 of the present embodiment may have a lining portion 405 and a closure feature 410. The lining portion 405 may be sized to extend over the side faces 110a-110d of the container 100 and line the inner portion 125. In some embodiments, the liner 400, including the lining portion 405 and the closure feature 410, may have all the physical aspects and functionalities of the liner 300, lining portion 305 and closure feature 310 described above in relation to FIGS. 3A-3F, and thus those aspects will not be repeated.

In the present embodiment, the liner 400 may be coupled to first and/or second covers 420, 435 along a first edge 401 of the liner. The first cover 420 may have a cover portion 425 and a closure feature 430, and the second cover 435 may have a cover portion 440 and a closure feature 445. In embodiments, the covers 420, 435 may be formed of a flexible material, such as a single plastic sheet, and may be sized to cover the opening of the container 100. The flexible material may allow for the first and second cover 420, 435 to extend across the container 100, e.g., the first and/or second cover 420, 435 may form a barrier across the second open end 120 of the container 100. In embodiments, the first and/or second cover 420, 435 may be at least partially substantially transparent or translucent, may be different colors, and/or may include symbols, patterns and/or words to indicate the status of the medical device. As such, the first and second covers 420, 435 may have similar features and functionalities relating to providing information about the clean or used status of a contained medical device, as has been described in relation to the first and second covers 320, 335 of FIGS. 3A-3F. As such those aspects will not be repeated.

The first and/or second covers 420, 435 may be coupled to each other and/or to the liner 400 along the first edge 401 of the liner. As such, the first and second covers 420, 435 may be pivotable about the first edge 401 to move between a covered position (i.e., one that seals off the inner portion 125 of the container 100) and an open position that allows a user to access the inner portion of the container. Each of the first and second covers 420, 435 can be fixed in place via their respective closure features 430, 445. The closure features 430, 445 comprise tab members 432, 447 that extend from the respective first and second cover 420, 435 on a side opposite the first edge 401.

In some embodiments the tab members 432, 447 may include an adhesive on a container-facing side thereof. This adhesive may allow the user to press the tab member 432, 447 against the associated side 110a-110d of the container 100 to fix the tab member 432, 447 to the side of the container, thus maintaining the cover 420, 435 in place over the container 100. In some embodiments the adhesive may allow the tab member 432, 447 to be removably fixed to the side face 110a-110d of the container 100 or another portion of the liner 400 so that the tab member 432, 447 can be released from the side of the container or another portion of the liner to release the cover from the container. The tab member 432, 447 may, in some embodiments, be elastic so that it is at least partially extensible to fix the cover 420, 435 to the container.

In some embodiments the first cover 420 may be selectively removable from the second cover 435 and/or the liner. In one non-limiting example embodiment, the first cover 420 may perforated at or near the location of its attachment to the second cover 435 and/or liner 400 so that it can be removed by a user. The first cover 420 may also be positioned over the second cover 435 so that when the first cover 420 is in a closed position with respect to the container 100, the second cover 435 is covered by the first cover 420.

In use, the second cover 435 may be pivoted about the first edge 401 so that it nests within the inner portion 125 of the container 100. A clean medical device 403 can be placed within the container 100, on top of the second cover 435 (see FIG. 4B). The first cover 420 can be pivoted about the first edge 401 so that it covers the inner portion 125 of the container 100 and the medical device 403. The adhesive of the tab member 432 can be exposed, and the tab can be adhered to a side 110a-110d of the container 100 to fix the tab member 432 to the side of the container, thus maintaining the first cover 420 in place over the container 100.

The tab member 432 can be detached from the side 110a-110d of the container 100 and the first cover can be pivoted back, about the first edge 401, to allow a user to access the clean medical device 403. The first cover 420 can be detached from the liner 400 and/or the second cover 435 along the perforation. After the medical device 403 has been used, the second cover can be pivoted back, about the first edge 401, to allow the user to return the used medical device 403 to the container 100. The used medical device can be placed within the inner portion 125 of the container 100, on top of the liner 400 (see FIG. 4C). The second cover 435 can be pivoted about the first edge 401 so that it covers the inner portion 125 of the container 100 and the used medical device 403. The adhesive of the tab 447 can be exposed, and the tab can be adhered to a side 110a-110d of the container 100 to fix the tab member 447 to the side of the container, thus maintaining the second cover 435 in place over the container 100.

In one non-limiting example embodiment, after endoscope reprocessing, a clean medical device 403 may be placed in a lined container, and the first cover 420 may be extended across the second open end 120, which may be green in color. The container may be transported from a reprocessing location to a medical procedure location, where the clean medical device may be used on a patient. Subsequent to the procedure, the used medical device may be placed back in the container, and the second cover 435 may be extended across the second open end 120, which may be red in color. This may indicate to a medical professional, or other medical facility personnel that the medical device should be transported back to the reprocessing area for cleaning.

Similar to the liner 400, the first and/or second cover 420, 435 may enclose the side faces 110a-110d, as well as the already-attached liner 400. By aligning the first cover 420 to extend across the inner portion 125 of the container 100, a clean medical device may be protected from outside contamination. Additionally, a used medical device, which may include contaminants from a patient, may be containable by the second cover 435, and the liner 400.

Referring now to FIGS. 5A-5D, an embodiment of a liner and cover arrangement will be described in greater detail. The liner 500 of the present embodiment may have a lining portion 505 and a closure feature 510. The lining portion 505 may be sized to extend over the side faces 110a-110d of the container 100 and line the inner portion 125. In some embodiments, the liner 500, including the lining portion 505 and the closure feature 510, may have all the physical aspects and functionalities of the liner 300, lining portion 305 and closure feature 310 described above in relation to FIGS. 3A-3F, and as such those aspects will not be repeated.

Figure 5A:
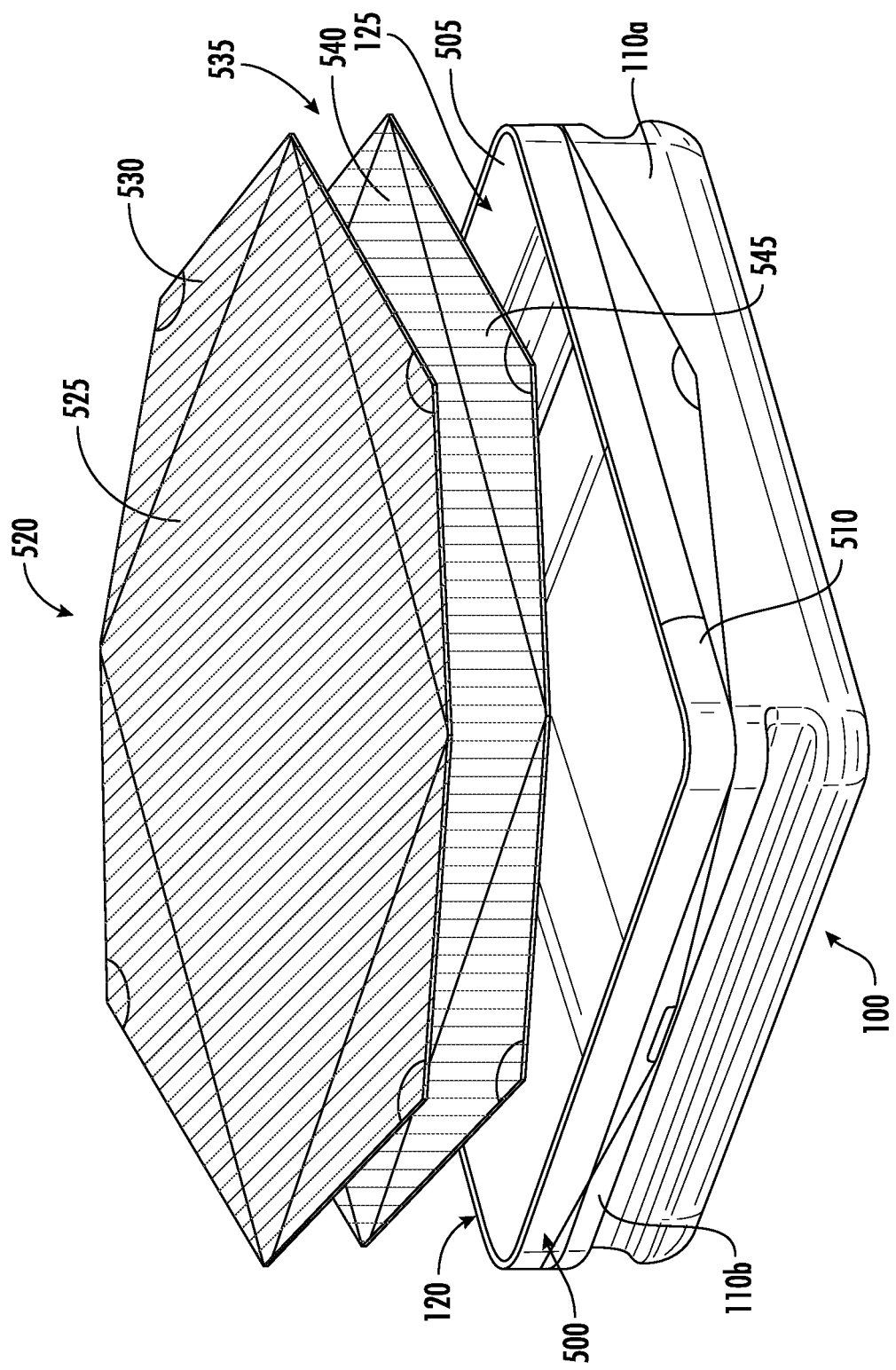
Figure 5B:
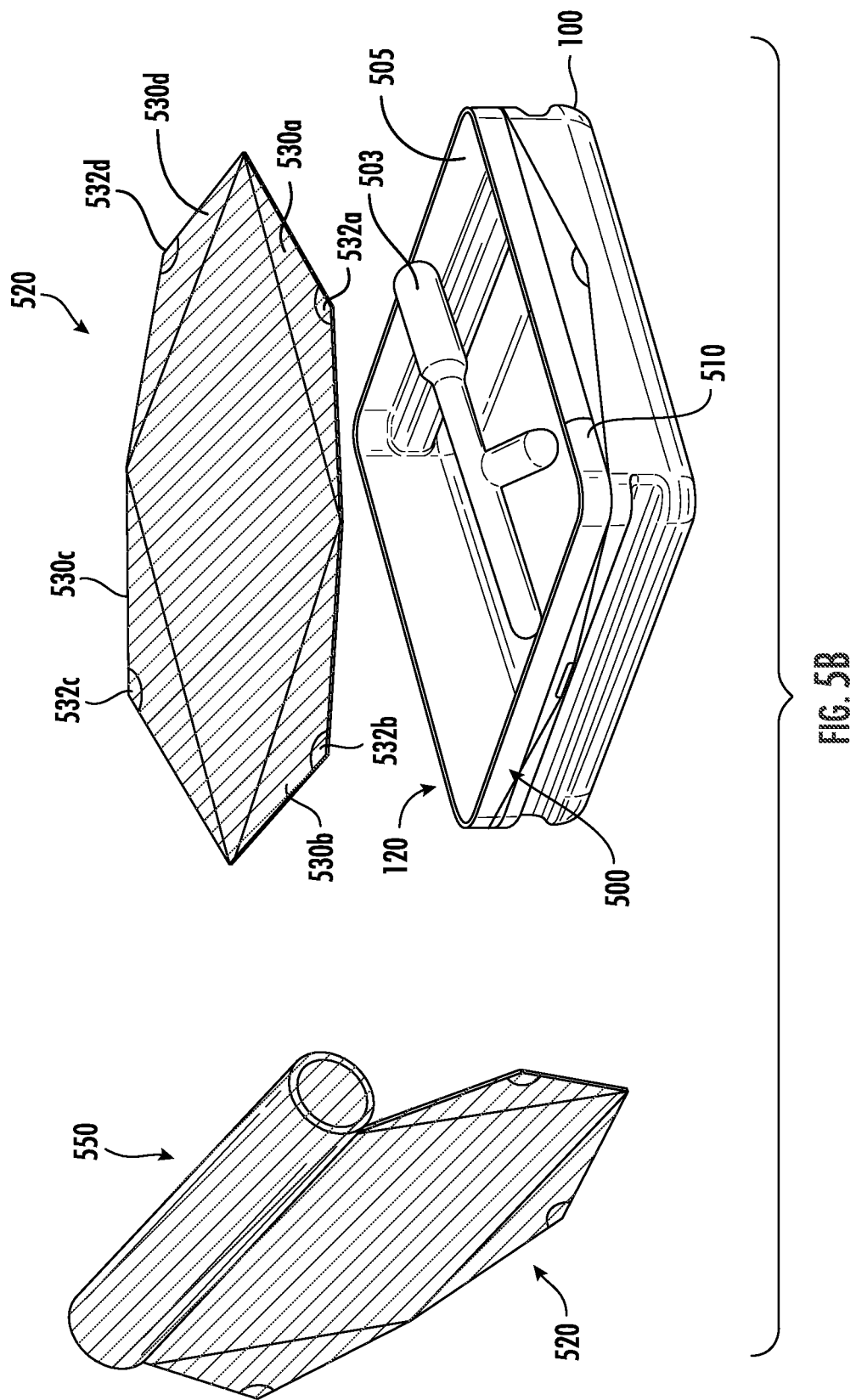
Figure 5C:
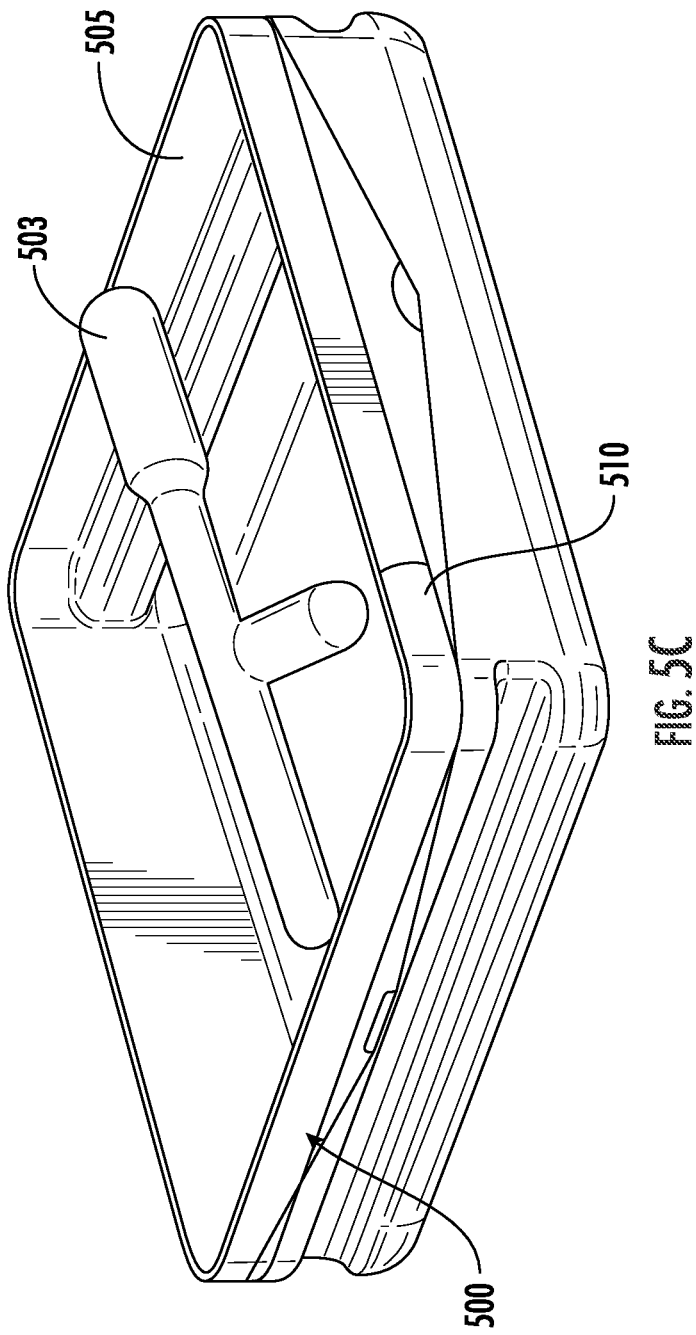

The liner 500 may be removably attachable to the container 100 prior to placement of a medical device 503 in the inner portion 125 of the container. As shown in FIG. 5B, a medical device 503 may be placed in an inner portion 125 of a container 100 after the liner 500 is attached to the container. When the medical device 503 is placed in the container 100, a cover may be extendable across the second open end 120, so that the medical device is captured between the liner 500 and the cover. A first cover 520 may have a cover portion 525 and a closure feature 530, and a second cover 535 may have a cover portion 540 and a closure feature 545. In embodiments, the first and second covers 520, 535 may be formed of a flexible material, such as a single plastic sheet. The flexible material may allow for the first and second covers 520, 535 to extend across the container 100, e.g., the first and/or second cover 520, 535 may form a barrier across the second open end 120 of the container 100. In embodiments, the first and/or second cover 520, 435 may be at least partially substantially transparent or translucent. It is also envisioned that the first and second covers 520, 535 may be different colors, and/or may include symbols, patterns and/or words to indicate the status of the medical device. Thus, the first and second covers 520, 535 may have similar features and functionalities relating to providing information about the clean or used status of a contained medical device, as has been described in relation to the first and second covers 320, 335 of FIGS. 3A-3F. As such those aspects will not be repeated.

The first and/or second covers 520, 535 may be removably attachable to the container by the respective closure feature 530, 545, so that the covers 520, 535 are substantially taut (e.g., the covers may not sag into the inner portion 125 of the container) across the second open end 120. The first and/or second covers 520, 535 may be exchangeable with each other, e.g., by the medical professional. For example, after endoscope reprocessing, a clean medical device 503 may be placed in a lined container, and a first cover 520 may be extended across the second open end 120, which may be green in color. The container may be transported from a reprocessing location to a medical procedure location, where the clean medical device may be used on a patient. Subsequent to the procedure, the used medical device may be placed back in the container, and a second cover 535 may be extended across the second open end 120, which may be red in color. This may indicate to a medical professional, or other medical facility personnel that the medical device should be transported back to the reprocessing area for cleaning.

Similar to the liner 500, the first and/or second cover 520, 535 may enclose a portion of the side faces 110a-110d, as well as the already-attached liner 500. By aligning the first and second covers 520, 535 so that the cover portions 525, 540 may be continuously extended across the inner portion 125 of the container 100, a clean medical device may be protected from outside contamination. Additionally, a used medical device, which may include contaminants from a patient, may be containable by the first and second covers 520, 535, and the liner 500.

In some embodiments, the cover portions 525, 540 may have the same size and shape as the second open end 120 of the container 100. The respective closure features 530, 545 may be extensions of the first and second cover portions 525, 540. In the illustrated embodiment the closure features 530, 545 may comprise extension portions 530a-d, 545a-d (see FIGS. 5B, 5D) (which may also be referred to as tabs or tab portions) that extend beyond the edges of the cover portions 525, 540 so that when the first and second covers 520, 535 are placed over the second open end 120 of the container, the extension portions extend over the side faces 110a-110d of the container 100. The extension portions 530a-d, 545a-d may include an adhesive region 532a-d, 547a-d on a container-facing side thereof. This adhesive region may allow the user to press the extension portions 530a-d, 545a-d against the associated side 110a-110d of the container 100 to fix the extension portions 530a-d, 545a-d to the side of the container, thus maintaining the cover 520, 535 in place over the second open end 120 of the container 100. In some embodiments the adhesive regions 532a-d, 547a-d may allow the extension portions 530a-d, 545a-d to be removably fixed to the side face 110a-110d of the container 100 or another portion of the liner 500 so that the extension portions 530a-d, 545a-d can be released from the side of the container or another portion of the liner to release the respective cover 520, 535 from the container. The extension portions 530a-d, 545a-d may, in some embodiments, be elastic so that it is at least partially extensible to fix the cover 520, 535 to the container.

In some embodiments, the first and second covers 520, 535 can be dispensed from respective rolls 550, 555, each of which contain a plurality of covers that can be dispensed serially as needed by the user. It will be appreciated that the adhesive regions 532a-d, 547a-d may be embodied in a "peel and stick" arrangement in which removable tabs (not shown) are disposed over the adhesive regions to prevent the first and second covers 520, 535 from adhering to each other while in the rolled state. The use can simply pull the removable tabs off the adhesive regions 532a-d, 547a-d to apply a cover 520, 535 to the container 100.

It will be understood that although extension portions 530a-d, 545a-d and adhesive regions 532a-d, 547a-d are disclosed for coupling the first and second covers 520, 535 to the container 100, it is also contemplated that the first and/or second covers 520, 535 may be removably attachable to the container 100 in any manner, including but not limited to an elastic, a drawstring, an adhesive, hook-and-loop fasteners, or the like. In addition, although the first and second covers 520, 535 are disclosed as being separate pieces, they could instead be pre-bonded together, and simply flipped over after use.

In use, a clean medical device 503 can be placed within the container 100, on top of the liner 500 (see FIG. 5B). The first cover 520 can be dispensed from the roll 550 and placed over the container 100 so that it covers the inner portion 125 of the container 100 and the medical device 503. The adhesive regions 532a-d of the extension portions 530a-d can be exposed, and the extension portions can be adhered to respective sides 110a-110d of the container 100 to fix the extension portions to the sides of the container, thus maintaining the first cover 520 in place over the container 100 and the medical device.

The extension portions 530a-d can be detached from the sides 110a-110d of the container 100 and the first cover 520 can be removed, to allow a user to access the clean medical device 503. The first cover 520 can then be disposed of. After the medical device 503 has been used, the used medical device can be placed within the inner portion 125 of the container 100, on top of the liner 500 (see FIG. 5C). The second cover 535 can be dispensed from the roll 555 and placed over the container 100 so that it covers the inner portion 125 of the container 100 and the medical device 503. The adhesive regions 547a-d of the extension portions 545a-d can be exposed, and the extension portions can be adhered to respective sides 110a-110d of the container 100 to fix the extension portions to the sides of the container, thus maintaining the second cover 535 in place over the container 100 and the medical device.

In one non-limiting example embodiment, after medical device reprocessing, a clean medical device 503 may be placed in a lined container, and the first cover 520 may be extended across the second open end 120, which may be green in color. The container 100 may be transported from a reprocessing location to a medical procedure location, where the clean medical device may be used on a patient. Subsequent to the procedure, the used medical device may be placed back in the container 100, and the second cover 535 may be extended across the second open end 120, which may be red in color. This may indicate to a medical professional, or other medical facility personnel that the medical device should be transported back to the reprocessing area for cleaning.

Similar to the liner 500, the first and/or second cover 520, 535 may enclose a portion of the side faces 110a-110d of the container 100, as well as the already-attached liner 500. By aligning the first cover 520 to extend across the inner portion 125 of the container 100, a clean medical device may be protected from outside contamination. Additionally, a used medical device, which may include contaminants from a patient, may be containable by the second cover 535, and the liner 500.

Figure 6A:
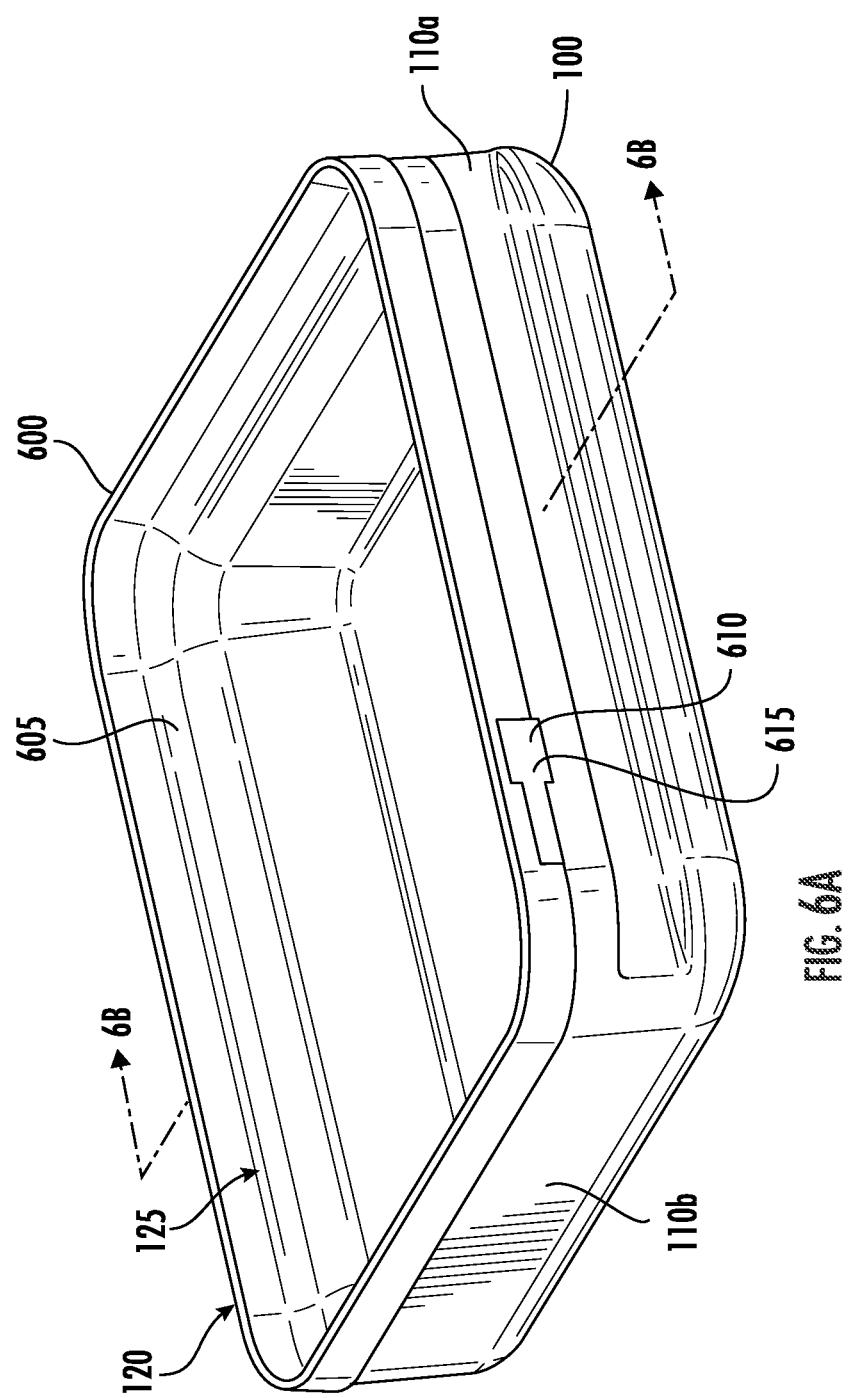

Referring now to FIGS. 6A-6D, an embodiment of a liner and cover arrangement will be described in greater detail. The liner 600 may have a lining portion 605 and a closure feature 610. The lining portion 605 may be sized to extend over the side faces 110a-110d of the container 100 and line the inner portion 125. The lining portion 605 may enclose a portion of the container 100 to act as a protective barrier and prevent and/or minimize direct contact between a medical device and the container, and/or between a user and the medical device and/or container. The lining portion 605 may be formed of a flexible thermoformed material that closely conforms to the surfaces forming the inner portion 125 of the container 100. Such conformity is best seen in FIG. 6B. By providing a thermoformed liner 600, additional slack material that can be present when the liner is formed as a bag can be eliminated.

A portion of the liner 600 may surround the side faces 110a-110d and may sit in the inner portion 125 of the container. In embodiments, the liner 600 may be at least partially substantially transparent or translucent, although it is also envisioned that the liner 600 may be colored, or opaque. The liner 600 may be removably attachable to the container by the closure feature 610, so that when the container 100 is lined, the closure feature 610 maintains the liner 600 in position and to enclose the container 100. By fitting the liner 600 into the inner portion 125 of the container 100, contamination of the container may be minimized.

In embodiments, the closure feature 610 may be a pull-tab 615 that can be removably fixed to a surface of the container 100 once the liner 600 has been fit into the inner portion 125 of the container and cinched around the side faces 110a-110d of the container. The liner 600 may be fit into the container 100 with the pull-tab 615 in an un-extended position. Once the liner 600 is positioned to enclose the container 100, the pull-tab 615 may be moved to an extended position, thereby cinching the liner 600 around the side faces 110a-110d of the container. An adhesive may be provided on a container-facing side of the pull-tab 615. This adhesive may allow the user to press the pull-tab 615 against the associated side 110a-110d of the container 100 to fix the pull-tab 615 to the side of the container, thus maintaining the liner 600 cinched around the container. In some embodiments the liner 600 may be configured so that the adhesive applied to the pull-tab 615 fixes the pull-tab to another portion of the liner, thus maintaining the liner cinched around the container 100. In some embodiments the adhesive may allow the pull-tab 615 to be removably fixed to the side faces 110a-110d of the container 100 or another portion of the liner 600 so that the pull-tab 615 can be released from the side of the container or another portion of the liner to release the liner from the container after use. The pull-tab 615 may, in some embodiments, be elastic so that it is at least partially extensible when configured in the extended state.

Although a pull-tab closure is illustrated in FIGS. 6A-6D, it will be understood that the liner 600 may be removably attachable to the container 100 in any manner, including but not limited to an elastic, a drawstring, an adhesive, hook-and-loop fasteners, or the like.

Figure 6D:
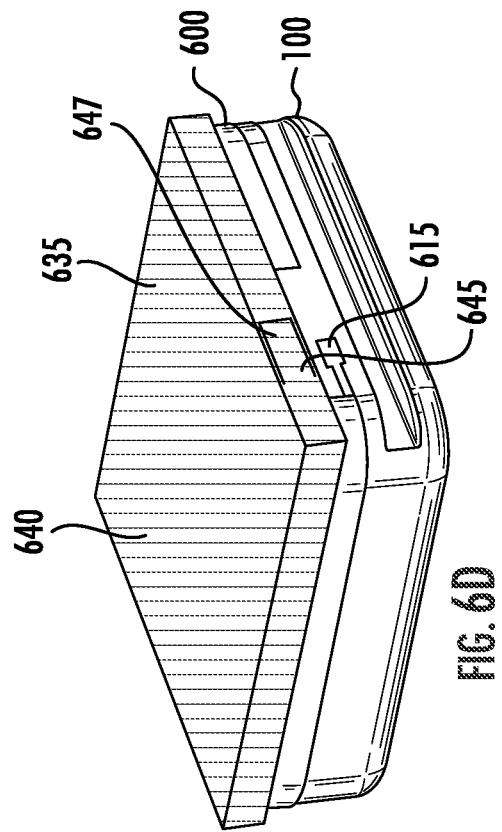
Figure 6C:
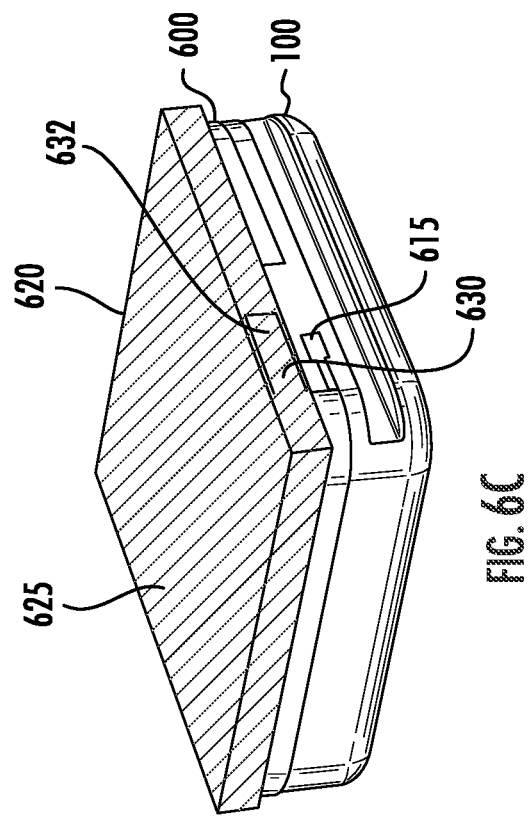

As described, the liner 600 may be removably attachable to the container 100 prior to placement of medical device in the inner portion 125 of the container. A medical device (not shown) may be placed in an inner portion 125 of a container 100 after the liner 600 is attached to the container. When the medical device is placed in the container 100, a cover may be extendable across the second open end 120 (FIG. 6A), so that the medical device is captured between the liner 600 and the cover. Referring to FIGS. 6C and 6D, a first cover 620 may have a cover portion 625 and a closure feature 630, and a second cover 635 may have a cover portion 640 and a closure feature 645. In embodiments, the covers 620, 635 may be formed of a flexible material, such as a single plastic sheet, and may have an edge as the respective closure feature 630, 645. The flexible material may allow for the first and second cover 620, 635 to extend across the container 100, e.g., the first and/or second cover 620, 635 may form a barrier across the second open end 120 of the container 100. In embodiments, the first and/or second cover 620, 435 may be at least partially substantially transparent or translucent. As such, the first and second covers 620, 635 may have similar features and functionalities relating to providing information about the clean or used status of a contained medical device, as has been described in relation to the first and second covers 320, 335 of FIGS. 3A-3F. As such those aspects will not be repeated The first and/or second covers 620, 635 may be removably attachable to the container by the respective closure feature 630, 645, so that the covers 620, 635 are substantially taut (e.g., the covers may not sag into the inner portion 125 of the container) across the second open end 120. The first and/or second covers 620, 635 may be exchangeable with each other, e.g., by the medical professional. For example, after medical device reprocessing, a clean medical device (not shown) may be placed in a lined container, and a first cover 620 may be extended across the second open end 120, which may be green in color. The container 100 may be transported from a reprocessing location to a medical procedure location, where the clean medical device may be used on a patient. Subsequent to the procedure, the used medical device may be placed back in the container, and a second cover 635 may be extended across the second open end 120, which may be red in color. This may indicate to a medical professional, or other medical facility personnel that the medical device should be transported back to the reprocessing area for cleaning.

Similar to the liner 600, the first and/or second cover 620, 635 may enclose the side faces 110a-110d, as well as a portion of the already-attached liner 600. By aligning the first and second covers 620, 635 so that the cover portions 625, 640 may be continuously extended across the inner portion 125 of the container 100, a clean medical device may be protected from outside contamination. Additionally, a used medical device, which may include contaminants from a patient, may be containable by the first and second covers 620, 635, and the liner 600. For example, fluids or other particulates may not leak over the closure feature 630, 645 when positioned on the outer surface 148 of the bottom face 105.

In embodiments, the first and second covers 620, 635 may be removably attachable to the container 100 by respective closure features 630, 645, so that when the container 100 is covered, the associated closure features 630, 645 maintain the covers 620, 635 in position with respect to the container 100. In embodiments, the closure features 630, 645 can be pull-tabs 632, 647 that can be removably fixed to a surface of the container 100 once the respective cover 620, 635 has been cinched around the side faces 110a-110d (FIG. 1A) of the container. The selected cover 620, 635 may be placed over the container 100 with the pull-tabs 632, 647 in an un-extended position. Once the cover 620, 635 is positioned to enclose the container 100, the pull-tab 632, 647 may be moved to an extended position, thereby cinching the cover 620, 635 around the side faces 110a-110d of the container.

In some embodiments, an adhesive may be provided on a container-facing side of each pull-tab 632, 647. This adhesive may allow the user to press the pull-tab 632, 647 against the associated side 110a-110d of the container 100 to fix the pull-tab 632, 647 to the side of the container, thus maintaining the cover 620, 635 cinched around the container. In some embodiments the cover 620, 635 may be configured so that the adhesive applied to the pull-tab 632, 647 fixes the pull-tab to a portion of the liner 600, thus maintaining the cover 620, 635 cinched around the container 100. In some embodiments the adhesive may allow the pull-tab 632, 647 to be removably fixed to the side faces 110a-110d of the container 100 or a portion of the liner 600 so that the pull-tab 632, 647 can be released from the side of the container or the liner to release the cover 620, 635 from the container after use. The pull-tab 632, 647 may, in some embodiments, be elastic so that it is at least partially extensible when configured in the extended state. Although a pull-tab closure is disclosed, it will be understood that the cover 620, 635 may be removably attachable to the container 100 in any manner, including but not limited to an elastic, a drawstring, an adhesive, hook-and-loop fasteners, or the like.

In some embodiments, the first and/or second cover 620, 635 can be form fitting to the shape of the container 100 so that when the first and/or second cover 620, 635 is fit over the container, the cover(s) fit snugly to the side faces 110a-110d of the container 100 (FIG. 1) even before the respective pull-tab 632, 647 is extended and fixed to one of the side faces of the container or the liner 600. In other embodiments, the first and/or second cover 620, 635 is slightly oversized or is bag-shaped so that it can be easily placed over the container 100 to provisionally cover the container. In such embodiments, the pull-tab 632, 647 may be extended and adhered to the side of the container 100 or the liner 300 to cinch the cover 620, 635 to the container.

Referring now to FIGS. 7A-7D, an embodiment of a single use container and cover arrangement will be described in greater detail. In the illustrated embodiment, a discrete liner is not provided because the container itself is configured for disposal after use (i.e., it will not be cleaned and reused). Thus, in the present embodiment the container and the liner may be a single integral piece (i.e., the container itself performs the function of the liner). The container 1000 may incudes some or all of the features of the container 100 described in relation to FIGS. 1A-1I and may further include a laterally extending ledge portion 1100 disposed about the perimeter of the second open end 1120. The ledge portion 1100 can provide a flat surface for receiving a removable cover.

As with the previously described arrangements, a medical device (not shown) may be placed in an inner portion 1125 of the container 1000. When the medical device is placed in the container 1000, a cover may be extendable across the second open end 1120, so that the medical device is captured between the container 1000 and the cover. Referring to FIGS. 7B-7D, a first cover 720 may have a cover portion 725 and a closure feature 730, and a second cover 735 may have a cover portion 740 and a closure feature 745. In embodiments, the covers 720, 735 may be formed of a flexible material, such as a single plastic sheet sized to match the size of the second open end 1120 of the container 1000. The flexible material may allow for the first and second cover 720, 735 to extend across the container 100, e.g., the first and/or second cover 720, 735 may form a barrier across the second open end 1120 of the container 1000. In embodiments, the first and/or second cover 720, 735 may be at least partially substantially transparent or translucent. It is also envisioned that the first and second covers 720, 735 may be different colors, and/or may include symbols, patterns and/or words to indicate the status of the medical device. As such, the first and second covers 720, 735 may have similar features and functionalities relating to providing information about the clean or used status of a contained medical device, as has been described in relation to the first and second covers 320, 335 of FIGS. 3A-3F. As such those aspects will not be repeated.

The first and/or second covers 720, 735 may be removably attachable to the container 1000 by the respective closure feature 730, 745, so that the covers 720, 735 are substantially taut (e.g., the covers may not sag into the inner portion 1125 of the container) across the second open end 1120. The first and/or second covers 720, 735 may be exchangeable with each other, e.g., by the medical professional. For example, after endoscope reprocessing, a clean medical device (not shown) may be placed in the container, and a first cover 720 may be extended across the second open end 120, which may be green in color. The container may be transported from a reprocessing location to a medical procedure location, where the clean medical device may be used on a patient. Subsequent to the procedure, the used medical device may be placed back in the container, and a second cover 735 may be extended across the second open end 1120, which may be red in color. This may indicate to a medical professional, or other medical facility personnel that the medical device should be transported back to the reprocessing area for cleaning.

The first and/or second covers 720, 735 may couple to the laterally extending ledge portion 1100 of the container 1000 to removably fix the cover to the container. In some embodiments, the portion of the first and/or second cover 720, 735 that couples to the ledge portion 1100 of the container 1000 may be referred to as a tab, or tab portion. By aligning the first and second covers 720, 735 so that the cover portions 725, 740 may be continuously extended across the inner portion 1125 of the container 1000, a clean medical device may be protected from outside contamination. Additionally, a used medical device, which may include contaminants from a patient, may be containable by the first and second covers 720, 735, and the container 1000.

In some embodiments, the closure feature 730, 745 may be an adhesive (FIG. 7D), which may be provided on a container-facing side of cover 720, 735. This adhesive may allow the user to press the cover 720, 735 against the laterally extending ledge portion 1100 of the container 1000 to fix the cover 720, 735 to the ledge portion, thus maintaining the cover coupled to the container. In some embodiments the adhesive may allow the cover 720, 735 to be removably fixed to the laterally extending ledge portion 1100 of the container 1000 so that the cover can be released from the container after use.

It will be appreciated that the adhesive of the closure feature 730, 745 may be embodied in a "peel and stick" arrangement in which removable tabs (not shown) are disposed over the adhesive to prevent the first and second covers 720, 735 from adhering to other surfaces before use.

To fix the cover 720, 735 to the container 1000 the user can simply pull the removable tabs off the adhesive to apply a cover 720, 735 to the container 100.

It will be understood that although adhesive is disclosed for coupling the first and second covers 720, 735 to the container 1000, it is also contemplated that the first and/or second covers 720, 735 may be removably attachable to the container 1000 in any manner, including but not limited to a drawstrings, elastics, hook-and-loop fasteners, or the like. In addition, although the first and second covers 720, 735 are disclosed as being separate pieces, they could instead be pre-bonded together, and simply flipped over after use.

Numerous specific details have been set forth herein to provide a thorough understanding of the embodiments. It will be understood by those skilled in the art, however, that the embodiments may be practiced without these specific details. In other instances, well-known operations, components, and circuits have not been described in detail so as not to obscure the embodiments. It can be appreciated that the specific structural and functional details disclosed herein may be representative and do not necessarily limit the scope of the embodiments.

Some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

It should be noted that the methods described herein do not have to be executed in the order described, or in any particular order. Moreover, various activities described with respect to the methods identified herein can be executed in serial or parallel fashion.

Although specific embodiments have been illustrated and described herein, it should be appreciated that any arrangement calculated to achieve the same purpose may be substituted for the specific embodiments shown. This disclosure is intended to cover any and all adaptations or variations of various embodiments. It is to be understood that the above description has been made in an illustrative fashion, and not a restrictive one. Combinations of the above embodiments, and other embodiments not specifically described herein will be apparent to those of skill in the art upon reviewing the above description. Thus, the scope of various embodiments includes any other applications in which the above compositions, structures, and methods are used.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A system for containing and transporting a medical device, the system comprising:
   a container including a bottom face and surrounding side faces as a closed first end and an open second end to form an inner portion for receiving and retaining the medical device;
   a liner removably attachable to the container, the liner extendable over a portion of the side faces to line the inner portion of the container;

a first cover removably attachable to the container, the first cover extendable over the liner and the container to encapsulate a medical device placed on the liner within the container; and
a pull-tab;
wherein the first cover is attached to the container via the pull-tab, which is removably attached to one of the side faces.

2. The system according to claim 1, wherein the liner is coupleable to one of the side faces by an adhesive pull-tab.

3. The system according to claim 1, wherein the pull tab is an adhesive pull-tab.

4. The system according to claim 3, wherein the pull-tab is an elastic pull-tab.

5. The system according to claim 3, wherein the cover and adhesive pull-tab are configured such that when the cover is extended over the liner and the container and the adhesive pull-tab is moved from an un-extended position to an extended position and attached, the cover is cinched to the side faces.

6. The system according to claim 1, further comprising:
a second cover removably attachable to the first cover and extendable over at least a portion of the side faces and across the open second end of the container to enclose the inner portion.

7. The system according to claim 6, wherein the first and second covers are coupled to the liner along an edge of the liner.

8. The system according to claim 6, wherein the first cover is perforated at or near a location of its attachment to the second cover so that the first cover is removable from the second cover.

9. The system according to claim 6, wherein the first cover is positionable over the second cover so that when the first cover is in a closed position with respect to the container the second cover is covered by the first cover.

10. The system according to claim 1, further comprising:
a second cover removably attachable to at least one of the liner and the side face of the container, and extendable across the open second end of the container to enclose the inner portion; and
wherein the first cover is exchangeable with the second cover for visual verification of a condition of the medical device.

11. The system according to claim 10, wherein:
the first cover comprises a first cover portion and a plurality of extensions that are extendable beyond edges of the first cover portion so that when the first cover is placed over the second open end of the container, the extension portions extend over the side faces of the container; and
the second cover comprises a second cover portion and a plurality of extensions that are extendable beyond edges of the second cover portion so that when the second cover is placed over the second open end of the container, the extension portions extend over the side faces of the container.

12. The system of claim 10, wherein each of the extensions of the first and second cover portions include an adhesive region on a container-facing side thereof, and wherein the adhesive regions allow the user to press the extension portions against an associated side of the container to fix the extension portions to the side of the container to maintain the first or second cover in place over the second open end of the container.

13. The system of claim 10, wherein the first cover portion is dispensable from a rolled tube containing a plurality of said first cover portions, and the second cover portion is dispensable from a rolled tube containing a plurality of said second cover portions.

14. The system of claim 1, wherein the liner is formed from a flexible thermoformed material that closely conforms to surfaces forming the inner portion of the container.

15. A system for containing and transporting a medical device, the system comprising:
a container including a bottom face and surrounding side faces as a closed first end and an open second end to form an inner portion for receiving and retaining the medical device;
a liner removably attachable to the container to line the inner portion of the container;
a first cover removably attachable to the liner or the container; and
a pull-tab;
wherein the first cover is attached to the container via the pull-tab, which is removably attached to one of the side faces to encapsulate a medical device placed on the liner within the container.

16. The system according to claim 15, wherein the pull-tab is an adhesive pull-tab.

17. The system according to claim 16, wherein the pull-tab is an elastic pull-tab.

18. The system according to claim 15, further comprising:
a second cover removably attachable to the first cover and across the open second end of the container to enclose the inner portion.

19. The system according to claim 18, wherein:
the first cover comprises a first cover portion and a plurality of extensions that are extendable beyond edges of the first cover portion so that when the first cover is placed over the second open end of the container, the extension portions extend over the side faces of the container; and
the second cover comprises a second cover portion and a plurality of extensions that are extendable beyond edges of the second cover portion so that when the second cover is placed over the second open end of the container, the extension portions extend over the side faces of the container; and
wherein the first cover has a first color or first marking indicating the medical device is clean, while a second cover has a second color or marking indicating the medical device is used.

20. A system for containing and transporting a medical device, the system comprising:
a container including a bottom face and surrounding side faces as a closed first end and an open second end to form an inner portion for receiving and retaining the medical device;
a liner removably attachable to the container to line the inner portion of the container; and
a first cover removably attachable to the liner or the container via a pull-tab that is removably attachable to one of the side faces to encapsulate a medical device placed on the liner within the container;
wherein the pull-tab is an adhesive pull-tab; and
wherein the cover and adhesive pull-tab are configured such that when the cover is extended over the liner and the container and the adhesive pull-tab is moved from an un-extended position to an extended position and attached, the cover is cinched to the side faces.

* * * * *